United States Patent [19]

Lauritzen

[11] Patent Number: 4,833,261

[45] Date of Patent: May 23, 1989

[54] ETHYLENE OXIDE PROCESS

[75] Inventor: Ann M. Lauritzen, Houston, Tex.

[73] Assignee: Shell Oil Company, Houston, Tex.

[21] Appl. No.: 185,749

[22] Filed: Apr. 25, 1988

Related U.S. Application Data

[62] Division of Ser. No. 926,026, Oct. 31, 1986, Pat. No. 4,761,394.

[51] Int. Cl.$^4$ .......................................... C07D 301/10
[52] U.S. Cl. .................................................... 549/536
[58] Field of Search ........................................ 549/536

[56] References Cited

U.S. PATENT DOCUMENTS

| | | | |
|---|---|---|---|
| 3,316,279 | 4/1967 | Fenton | 260/348.5 |
| 3,449,078 | 6/1969 | Quik et al. | 23/212 |
| 3,702,259 | 11/1972 | Nielsen | 117/37 R |
| 3,844,981 | 10/1974 | Cusumano | 252/471 |
| 3,962,136 | 6/1976 | Nielsen et al. | 252/454 |
| 3,962,285 | 6/1976 | Cusumano | 260/3485 R |
| 3,972,829 | 8/1976 | Michalko | 252/430 |
| 4,005,049 | 1/1977 | Fields | 252/467 |
| 4,010,115 | 3/1977 | Nielsen et al. | 252/454 |
| 4,012,425 | 3/1977 | Nielsen et al. | 260/3485 R |
| 4,242,235 | 12/1980 | Cognion | 252/455 R |
| 4,341,664 | 7/1982 | Antos | 252/466 PT |
| 4,342,667 | 8/1982 | Armstrong et al. | 252/476 |
| 4,350,616 | 9/1982 | Boussert | 252/463 |
| 4,356,312 | 10/1982 | Nielsen et al. | 549/534 |
| 4,459,372 | 7/1984 | Arema | 502/351 |
| 4,536,482 | 8/1985 | Carcia | 502/5 |
| 4,548,921 | 10/1985 | Geus et al. | 502/330 |

FOREIGN PATENT DOCUMENTS 0172565 2/1986 European Pat. Off. .
1325715 8/1973 United Kingdom .

Primary Examiner—W. J. Shine

[57] ABSTRACT

This invention relates to a process for the production of ethylene oxide by contacting ethylene with an oxygen-containing gas in the presence of a catalyst comprising silver, a promoter of an alkali metal and a promoter of rhenium supported on a porous refractory support.

103 Claims, 4 Drawing Sheets

ETHYLENE OXIDE PROCESS

This is a division of application Ser. No. 926,026 filed Oct. 31, 1986 now U.S. Pat. No. 4,761,394.

FIELD OF THE INVENTION

This invention relates to supported silver-based catalysts for the production of ethylene oxide.

BACKGROUND OF THE INVENTION

Supported silver catalysts have long been used in the conversion of ethylene and oxygen to ethylene oxide. The use of small amounts of the alkali metals, K, Rb and Cs, were noted as useful promoters in supported silver catalysts in U.S. Pat. Nos. 3,962,136, issued June 8, 1976 and 4,010,115, issued Mar. 1, 1977.

U.S. Pat. No. 3,844,981 issued Oct. 29, 1974, U.S. Pat. No. 3,962,285 issued June 8, 1976 and British Pat. No. 1,325,715, published Aug. 8, 1973, disclose the use of silver-rhenium ethylene oxide catalysts. In these patents a high surface area silver derivative such as silver oxide is impregnated with a rhenium solution and subsequently reduced to provide metallic rhenium alloyed with the silver. U.S. Pat. No. 3,762,285, patent discloses the use of KOH to precipitate $Ag_2O$ from $AgNO_3$. There is no disclosure in the patents of the use of suitable inert supports such as porous refractory supports. U.S. Pat. No. 4,584,921, issued Oct. 22, 1985, discloses the use of rhenium in silver-supported ethylene oxide catalysts. In this reference, the rhenium is first placed on the support in the form of finely divided metal particles and the silver is subsequently deposited on the outer surface of the particles. U.S. Pat. No. 3,316,279, issued Apr. 25, 1967, discloses the use of rhenium compounds, particularly ammonium and alkali metal perrhenate for the oxidation of olefins to olefin oxides. In this reference, however, the rhenium compounds are used unsupported along with a reaction modifier (cyanides, pyridines or quinolines) in a liquid phase reaction. U.S. Pat. No. 3,972,829, issued Aug. 3, 1976, discloses a method for distributing catalytically active metallic components on supports using an impregnating solution of catalyst precursor compound and an organic thioacid or a mercaptocarboxylic acid. Catalytically active metals include metals of Groups IVA, 1B, VIB, VIIB and VIII, including rhenium and which may be in either the oxidized or reduced state. However, promoting amounts of rhenium in combination with silver and promoter amounts of alkali metal on a porous refractory support are not suggested. U.S. Pat. No. 4,459,372, issued July 10, 1984, discloses the use of rhenium metal in combination with a surface metallated (using Ti, Zr, Hf, V, Sb, Pb, Ta, Nb, Ge and/or Si) alumina or silica. U.S. Pat. No. 4,005,049, issued Jan. 25, 1977, teaches the preparation of a silver/transition metal catalyst useful in oxidation reactions. In this instance, the silver serves as both a catalyst and a support for the transition metal cocatalyst. In U.S. Pat. No. 4,536,482, issued Aug. 20, 1985, catalytically active metals such as Ag and Re are cosputtered along with a cosputtered support material on a particular support. None of these references disclose the use of a promoting amount of rhenium which is present on a silver-based, alkali-doped supported catalyst.

SUMMARY OF THE INVENTION

This invention relates to a catalyst for the production of ethylene oxide from ethylene and molecular oxygen in the vapor phase which catalyst comprises a catalytically effective amount of silver, a promoting amount of alkali metal, and a promoting amount of rhenium supported on a porous refractory support. In a preferred embodiment, the alkali metal is a higher alkali metal of potassium, rubidium, cesium or mixtures thereof and is present in an amount ranging from about 20 to about 1500 ppm by weight of the total catalyst and the rhenium is present in an amount ranging from about 0.2 to about 5 millimoles of rhenium per kilogram of total catalyst. The rhenium may conveniently be a form of rhenium which is extractable in a dilute aqueous alkali metal hydroxide solution, particularly a 20 millimolar sodium hydroxide solution. In a preferred embodiment the instant combination of silver, alkali metal promoter, rhenium promoter and support affords higher selectivities, particularly higher initial selectivities to ethylene oxide at a given oxygen conversion level than is obtained under the same reaction conditions with the same combination of silver and support and none or one of the promoters selected from rhenium and alkali metal.

DETAILED DESCRIPTION OF THE INVENTION

Figure 1:
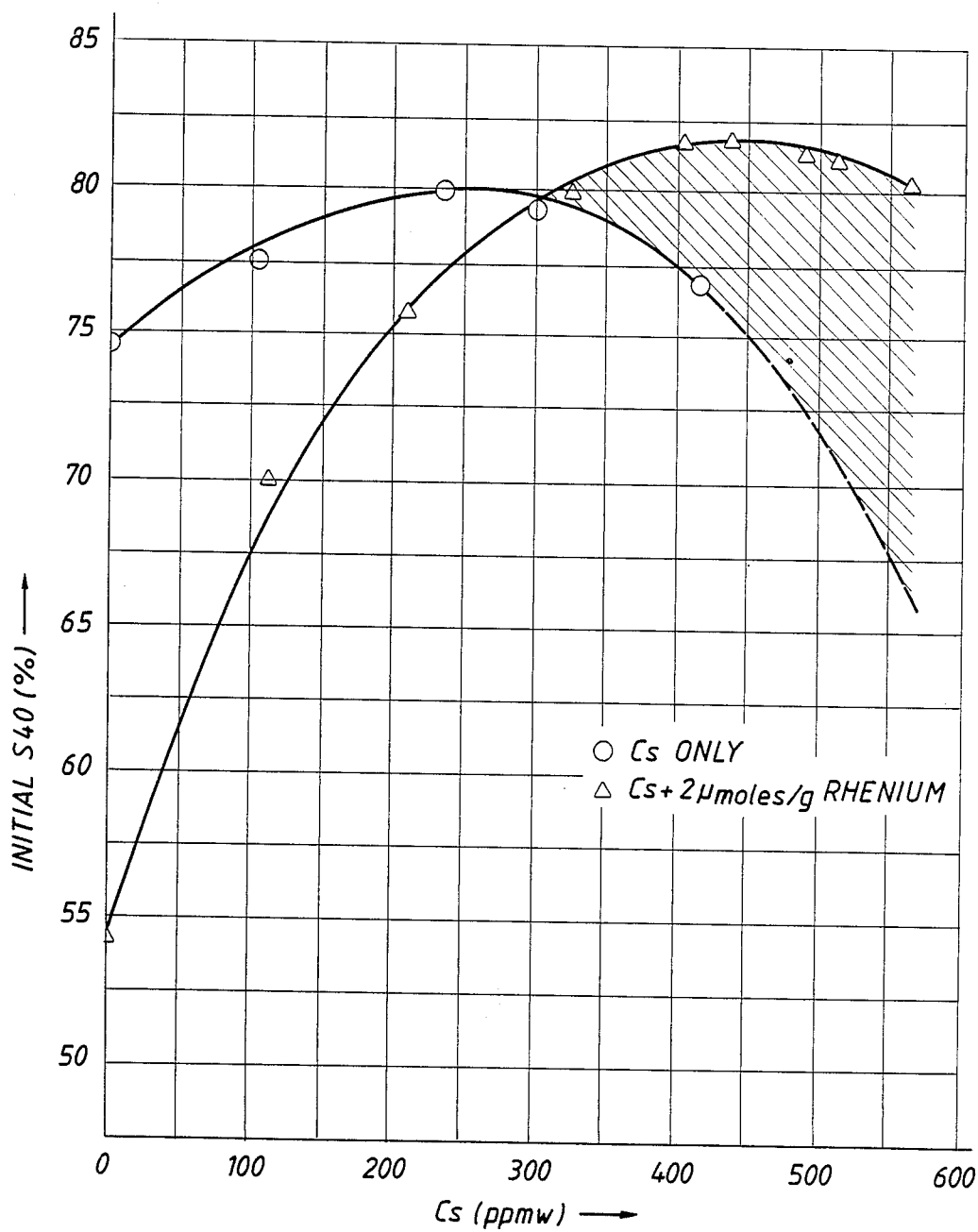
FIG. 1 shows optimized initial selectivity versus cesium promoter concentration for a catalyst of the instant invention containing rhenium and for a catalyst not containing rhenium thereby illustrating the enhanced initial selectivity obtained with the instant catalyst.
Figure 2:
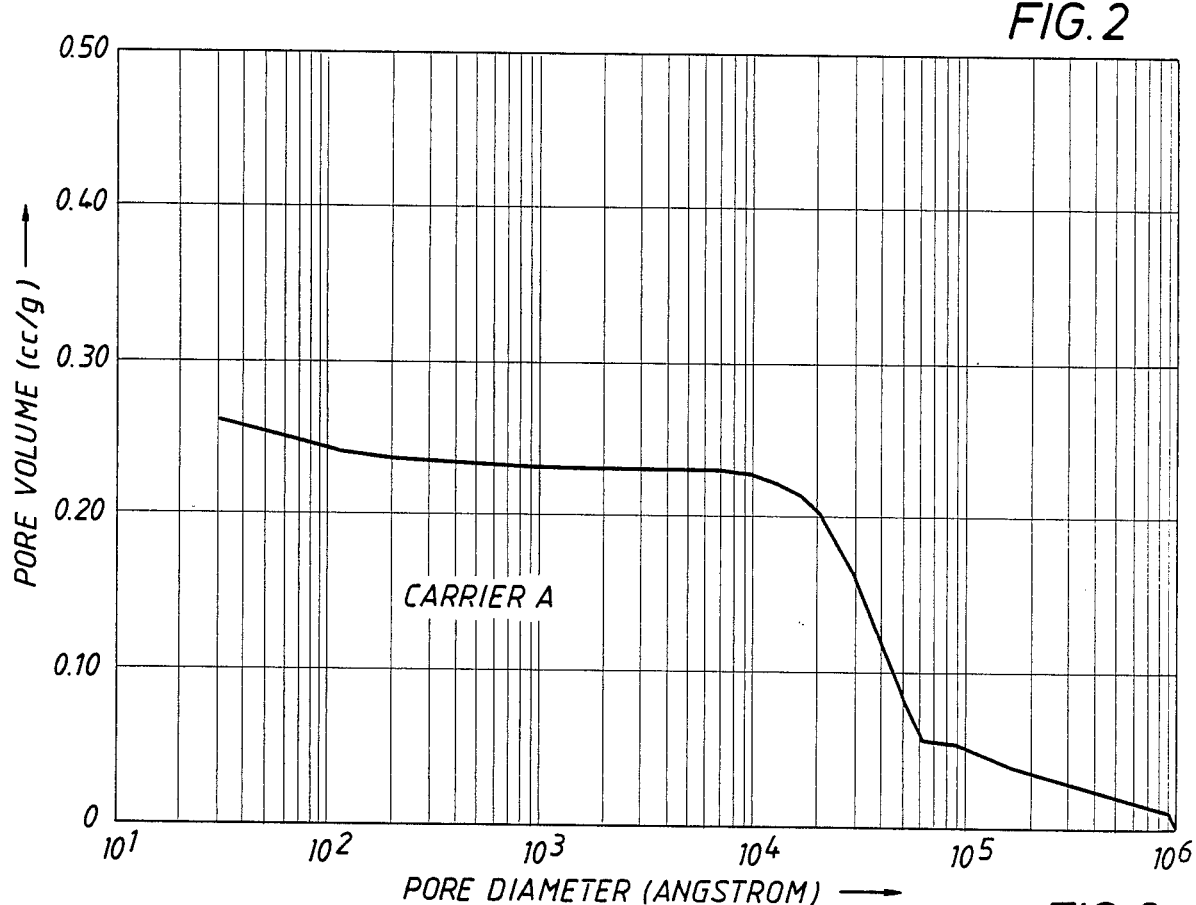
FIGS. 2–7 show pore size distribution curves for carriers A–F of Table I.
Figure 3:
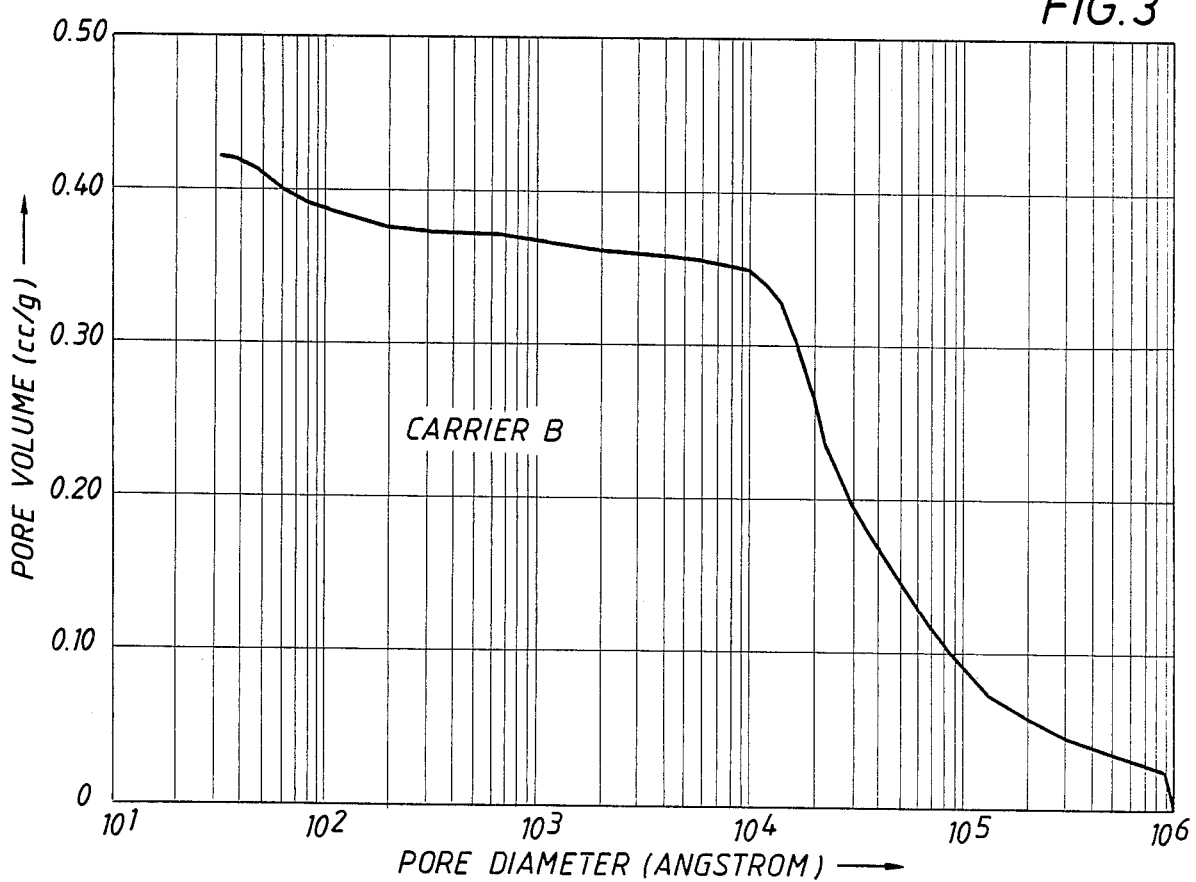
Figure 4:
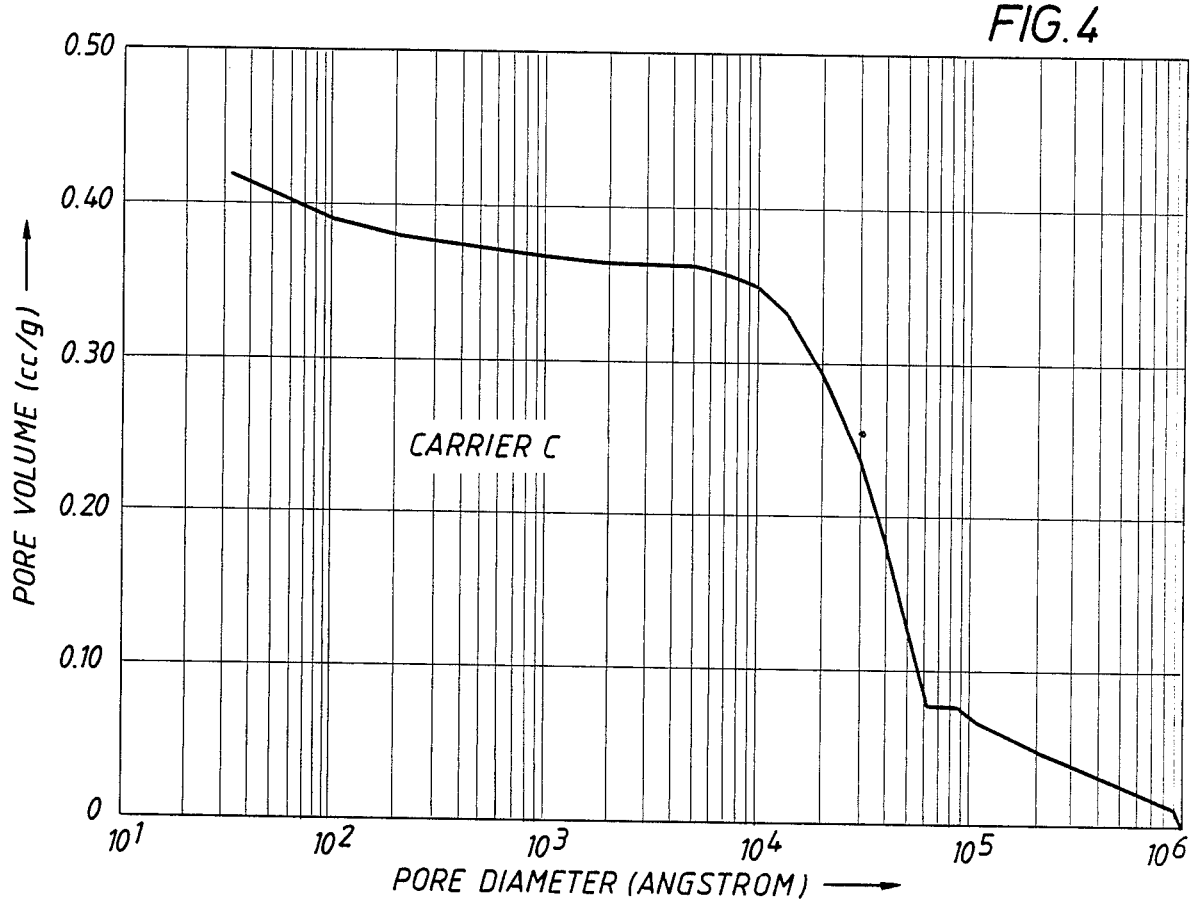
Figure 5:
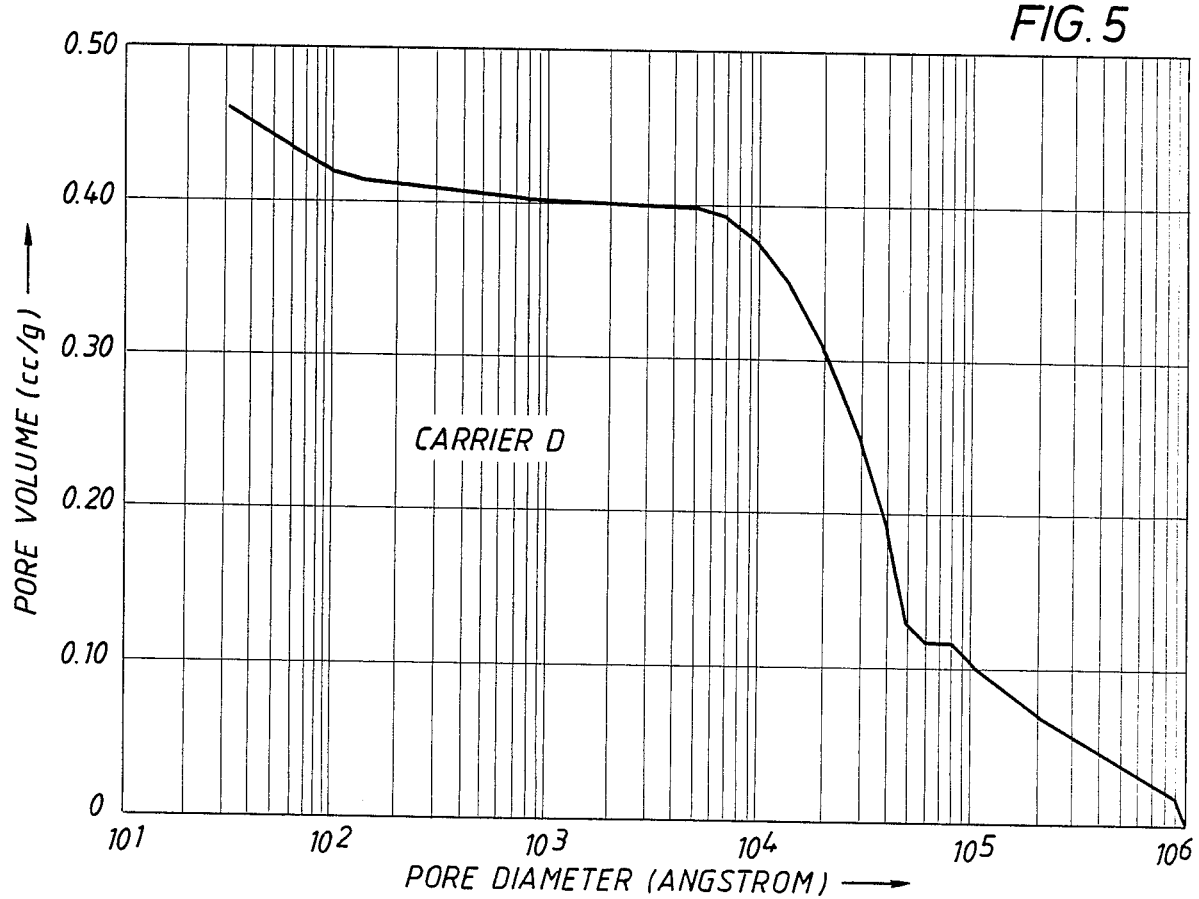
Figure 6:
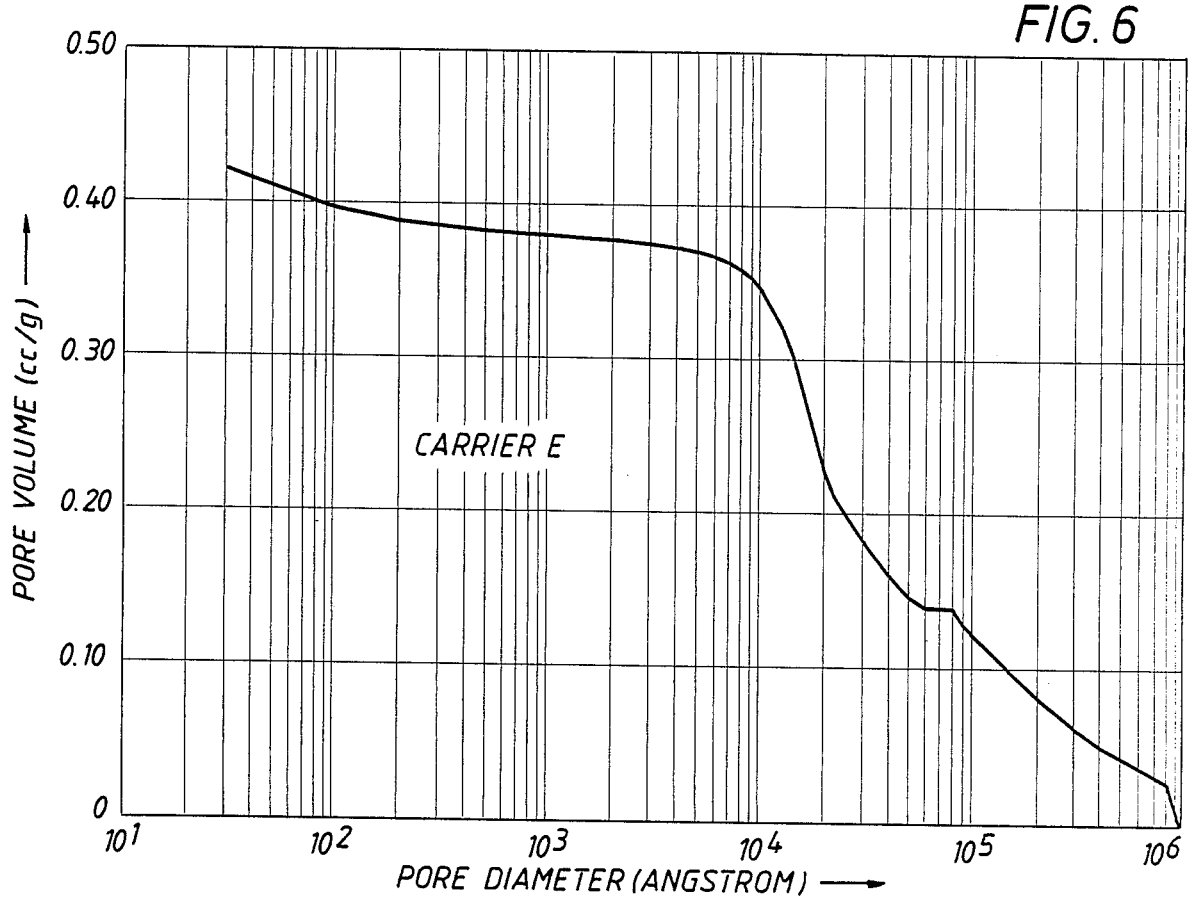
Figure 7:
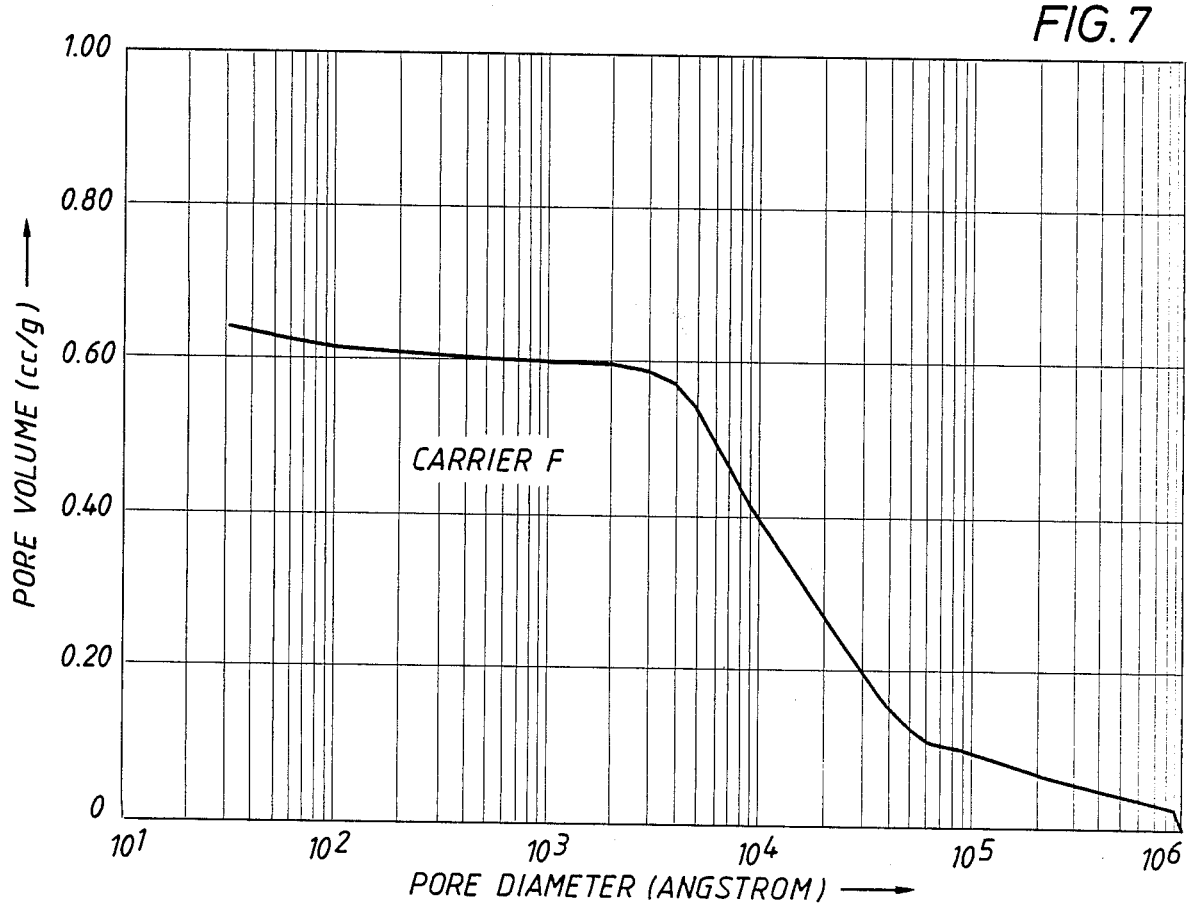

Generally, in the vapor phase reaction of ethylene with oxygen to produce ethylene oxide, the ethylene is present in at least a double amount (on a mol basis) compared with oxygen, but frequently is often much higher. Therefore the conversion is calculated according to the mol percentage of oxygen which has been used in the reaction. The oxygen conversion is dependent on the reaction temperature which latter is a measure of the activity of the catalyst employed. The value $T_{40}$ indicates the temperature at 40 mol percent conversion of the oxygen in the reactor and the value T is expressed in °C. This temperature is higher when the conversion of oxygen is higher. Moreover this temperature is strongly dependent on the employed catalyst and the reaction conditions. The selectivity (to ethylene oxide) indicates the molar amount of ethylene oxide in the reaction product compared with the total molar amount of ethylene converted. Herein the selectivity is indicated as $S_{40}$, which means the selectivity at 40 mol percent oxygen conversion. The selectivity of silver-based ethylene oxide catalysts can decrease over a period of time of usage. When comparing the selectivity performance of various silver-based ethylene oxide catalysts, it is important that the selectivity value be measured at approximately the same period of time of usage under the same or similar reaction conditions. As used herein, "initial selectivity" will refer to the selectivity of ethylene oxide catalysts when measured at a given constant oxygen conversion level of 40% at a gas hourly space velocity of approximately 3300 and when measured after the catalyst has been placed on stream for about 16±4 hours. Unless otherwise noted, all that are provided in the examples provided herein are initial selectivities.

In broad general terms the catalysts of the instant invention are prepared by impregnating porous refractory supports with silver ions, or compound(s), complex(es) and/or salt(s) dissolved in a suitable solvent sufficient to cause deposition on the support of from about 1 to about 25 percent by weight, basis total catalyst, of silver; the thus impregnated carrier is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier either prior to, coincidentally with, or subsequent to the deposition of the silver and/or alkali metal be suitable rhenium ions, or compound(s), complex(es) and/or salt(s) dissolved in a appropriate solvent. Detailed preparative techniques are discussed herein.

The support or carrier employed in these catalysts in its broadest aspects is selected from the larger number of conventional, porous refractory catalyst carriers or support materials which are considered relatively inert in the presence of the ethylene oxidation feeds, products and reaction conditions. Such conventional materials are known to persons skilled in the art and may be of natural or synthetic origin and preferably are of a macroporous structure, that is, a structure having a B.E.T. surface area below about 10 m²/g and preferably below about 3 m²/g. Very suitable supports comprise those of aluminous composition. Examples of supports that have been used as supports for different catalysts and which could, it is believed, be used as supports for ethylene oxide catalysts are the aluminum oxides (including the materials sold under the trade name "Alundum"), charcoal, pumice, magnesia, zirconia, keiselguhr, fullers' earth, silicon carbide, porous agglomerates comprising silica and/or silicon carbide, silica, magnesia, selected clays, artificial and natural zeolites and ceramics. Refractory supports particularly useful in the preparation of catalysts in accordance with this invention comprise the aluminous materials, in particular those comprising alpha alumina. In the case of alpha alumina-containing supports, preference is given to those having a specific surface area as measured by the B.E.T. method of from about 0.03 m²/g to about 10 m²/g, preferably from about 0.05 to about 5, more preferably from about 0.1 to about 3 m²/g, and a water pore volume as measured by conventional water absorption techniques of from about 0.1 to about 0.75 cc/g. The B.E.T. method for determining specific surface area is described in detail in Brunauer, S., Emmett, P. H. and Teller, E., *J. Am. Chem. Soc.*, 60, 309–16 (1938).

Certain types of alpha alumina-containing supports are particularly preferred. These alpha alumina supports have relatively uniform pore diameters and are more fully characterized by having (1) B.E.T. specific surface areas of from about 0.1 m²/g to about 3.0 m²/g, preferably about 0.1 m²/g to about 2.0 m²/g and (2) water pore volumes of from about 0.10 cc/g to about 0.75 cc/g, preferably from about 0.25 cc/g to about 0.55 cc/g. Typical properties of some supports found useful in the instant invention are shown in Table 1. Suitable manufacturers of carriers comparable to those in Table 1 include Norton Company and United Catalysts, Inc. (UCI).

TABLE 1

| Carrier | A | B | C | D | E | F |
|---|---|---|---|---|---|---|
| B.E.T. Surface Area, m²/g[a] | 0.21 | 0.42 | 0.42 | 0.48 | 0.57 | 2.06 |
| Water Pore Volume, cc/g | 0.26 | 0.36 | 0.41 | 0.49 | 0.44 | 0.65 |
| Crush Strength, FPCS, lbs[b] | 100% 20 lbs | 97% 15 | Avg 21 Range 15–30 | 90% 14 | 90% 15 | No Data |
| Total Pore Volume, Hg, cc/g[c] | 0.26 | 0.42 | 0.42 | 0.46 | 0.42 | 0.65 |
| Average Pore Diameter, Hg, Å[c] | 620 | 560 | 640 | 550 | 770 | 1000 |
| Median Pore Diameter, Hg, microns[c,e] | 3.7 | 2.7 | 3.4 | 3.4 | 2.4 | 2.5 |
| Percent Pore Volume in Pores Greater Than 350 Å[c] | 90.0% | 88.5% | 89.5% | 89.1% | 91.5% | 94.1% |
| Percent Pore Volume in Pores Greater Than 1 Micron[c] | 87.0% | 82.5% | 83.4% | 82.3% | 83.5% | 61.0% |
| % Wt. Alpha Alumina | 99.5 | 98 | 98.5 | 98.5 | 98 | 70–75 |
| Water Leachable Na, ppmw | 12 | 53 | 21 | 24 | 18 | No Data |
| Acid-Leachable Na, ppmw | 40 | 96 | 87 | 51 | 45 | No Data |
| Water-Leachable K, ppmw | 5 | 22 | 21 | 22 | 10 | No Data |
| Acid-Leachable Fe, ppmw | 2 | 5 | No Data | 1 | 5 | No Data |
| % Wt. SiO₂ | .5 | 2 | 1.5 | 15 | 2 | 25–30 |

[a]Method of Brunauer, Emmett and Teller, loc. cit.
[b]Flat Plate Crush Strength, single pellet.
[c]Determined by mercury intrusion to 55,000 psia using Micrometrics Autopore 9200 or 9210 (130° Contact angle, 0.473 N/m surface tension of Hg).
[e]Median pore diameter represents the pore diameter wherein 50% of the total pore volume is found in pores having less than (or greater than) the median pore diameter.

Pore size distribution curves measured by mercury intrusion techniques noted in footnote (c) above in Table 1 for carriers A–F are shown in FIGS. 2-7.

Of the carriers listed in Table 1, B and D are preferred because they provide catalysts which show better overall initial performance in terms of initial selectivity and initial activity.

Regardless of the character of the support or carrier used, it is preferably shaped into particles, chunks, pieces, pellets, rings, spheres, wagon wheels and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to employ a support formed into a rounded shape, such as for example, spheres, pellets, rings, tablets and the like, having diameters from about 0.1 inch to about 0.8 inch.

Particular supports may be selected having differing properties such as surface area and pore volume in order to provide particular catalytic properties. With regard to surface area (B.E.T.) possible lower limits are, for example, about 0.01, 0.03, 0.05, 0.075, 0.1, 0.15 and 0.2 $m^2/g$ and possible upper limits are, for example, about 0.6, 0.75, 0.9, 1, 2, 2.5, 3, 4, 5 and 10 $m^2/g$. With regard to water pore volume, possible lower limits are, for example, about 0.05, 0.1, 0.15, 0.2 and 0.35 cc/g and possible upper limits are, for example, about 0.5, 0.55, 0.6, 0.65, 0.7, 0.75 and 0.8 cc/g.

The catalysts of the instant invention are prepared by a technique in which the alkali metal promoters and the rhenium in the form of soluble salts and/or compounds are deposited on the catalyst and/or support prior to, simultaneously with, or subsequent to the deposition of the silver and each other. The alkali metal may be deposited at one step of the process and the rhenium at a different step or steps. The preferred method is to deposit silver, alkali metal and rhenium simultaneously on the support, that is, in a single impregnation step, although it is believed that the individual or concurrent deposition of the alkali metal and rhenium prior to and/or subsequent to the deposition of the silver produces suitable catalysts.

Although alkali metals exist in a pure metallic state, they are not in that form suitable for use. They are utilized as ions or salts or compounds of alkali metals dissolved in a suitable solvent for impregnation purposes. The porous carrier is impregnated with a solution of alkali metal promoter ions, salt(s) and/or compound(s) before, during or after impregnation or deposition of the silver ions, salt(s), complex(es) and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, silver content of the catalyst and the particular ions used in conjunction with the higher alkali metal cation or rhenium and amounts of rhenium present. The amount of alkali metal promoter deposited upon the support or present on the catalyst generally lies between about 10 and about 3000, preferably between about 15 and about 2000 and more preferably between about 20 and about 1500 parts by weight per million parts by weight of total catalyst. Most preferably, the amounts range between about 50 and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst and other compounds, cations or anions present in addition to alkali metal ions such as the ions added with the alkali metal or rhenium or compounds remaining from the impregnating solution, and the above-defined limits were selected to cover the widest possible variations in properties and characteristics. The effects of these variations are readily determined by experimentation. The alkali metal promoters are present on the catalysts in the form of cations (ions) or compounds or complexes or surface compounds or surface complexes rather than as the extremely active free alkali metals, although for convenience purposes only in this specification and claims they are referred to as "alkali metal" or "alkali metal promoters", even though not present on the catalyst as metals. For purposes of convenience the amount of alkali metal deposited on the support or present on the catalyst is measured as the metal rather than in the cationic or compound form. Thus, the alkali metal promoters are present on the support or catalyst in the form of cations (ions) or compounds or complexes or surface compounds or surface complexes. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture such as chlorides or carbonates or residual species from the impregnation solution(s).

In a preferred embodiment, at least a major proportion (greater than 50%) of the alkali metals is selected from the group consisting of potassium, rubidium, cesium and mixtures thereof.

In this preferred embodiment, the alkali metals comprise the higher alkali metals. As used herein the term "higher alkali metal" and cognates thereof refers to the alkali metals selected from the group consisting of potassium, rubidium, cesium and mixtures thereof. As used herein, the term "mixtures of alkali metals" or "mixtures of higher alkali metals" or cognates of these terms refers to the use of two or more of the alkali or higher alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. When the alkali metal comprises mixtures of higher alkali metals, at least two of the following are used, potassium, rubidium or cesium. Thus, for example, in the preferred embodiment wherein the higher alkali metal comprises potassium, rubidium, cesium or mixtures thereof, potassium may be used with cesium, or rubidium may be used with cesium, or potassium may be used with rubidium or all three may be used together. Hence, for example when potassium is used with cesium, the weight percent ration of potassium to cesium will range from 0/100 to 100/0, including all ranges in between such as 20/80, 50/50, 75/25 etc., and similar relationships will apply to other mixtures. A particularly preferred alkali metal promoter is cesium.

It must be clear that the amounts of alkali metal promoters on the catalysts are not necessarily the total amounts of these metals present in the catalyst. They are amounts that have been added to the catalyst by impregnation with suitable solutions of ions, salts and/or compounds and/or complexes of alkali metals. These amounts do not include amounts of alkali metals that are locked into the support, say by calcining, or are not extractable in a suitable solvent such as water or lower alkanol or amine or mixtures thereof and do not provide a promoting effort. It is also understood that the source of the alkali metal promoter ions, salts and/or compounds used to impregnate the catalyst may be the carrier. That is, the carrier may contain extractable amounts of alkali metal that can be extracted with a suitable solvent such as water or lower alkanol, thus preparing an impregnating solution from which the alkali metal ions, salts and/or compounds are deposited or redeposited on the support.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. It is understood that ions do not exist in vacuo, but are found in combination with charge-balancing counter ions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of nonlimiting example, oxides (containing only oxygen as the second element), hydroxides, nitrates, sulfates, carboxylates, carbonates, bicarbonates, oxyhalides, etc., as well as surface species wherein the element in question is bound directly or indirectly to an oxygen either in the substrate or on the surface.

As used herein, the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feed stock costs, energy costs, by-product removal costs and the like. The particular combination of silver, support, alkali metal and rhenium of the instant invention will provide an improvement in one or more catalytic properties over the same combination of silver and support and none or one of the promoters selected from rhenium and alkali metal.

As used herein, the term "catalytically effective amount of silver" refers to an amount of silver that provides a measurable conversion of ethylene and oxygen to ethylene oxide.

The carrier is also impregnated with rhenium ions, salt(s), compound(s) and/or complex(es). This may be done at the same time that the alkali metal promoter is added, before or later; or at the same time that the silver is added or before or later. Preferably rhenium, alkali metal and silver are in the same impregnating solution, although it is believed that their presence in different solutions will still provide suitable catalysts. The preferred amount of rhenium, calculated as the metal, deposited on or present on the carrier or catalyst ranges from about 0.1 mmoles to about 10 mmoles, more preferably from about 0.2 mmoles to about 5 mmoles per kilogram of total catalyst, or alternatively stated from about 19 to about 1860, more preferably from about 37 to about 930 parts by weight per million parts by weight of total catalyst. The degree of benefit obtained within the above-defined limits will vary depending upon particular properties and characteristics, such as, for example, reaction conditions, catalyst preparative conditions, surface area and pore structure and surface chemical properties of the carrier utilized, silver and alkali content of the catalyst, and other compounds, anions or cations present beside those containing rhenium or alkali metal, such as the ions added with the alkali metal or rhenium, or compounds remaining from the impregnation technique, and the above-defined limits were selected to cover the widest possible variations in properties and characteristics. These variations are readily determined by experimentation. For purposes of convenience, the amount of rhenium present on the catalyst is measured as the metal, irrespective of the form in which it is present.

The promoting effect provided by the rhenium can be affected by a number of variables such as, for example, reaction conditions, catalyst preparative techniques, surface area and pore structure and surface chemical properties of the support, the silver and alkali metal content of the catalyst, the presence of other compounds, cations and anions present on the catalyst alone or in combination with the alkali metal and/or rhenium such as the ions added with the alkali metal or rhenium, or compounds remaining from the impregnating solution. The presence of other activators, stabilizers, promoters, enhancers or other catalyst improvers can also affect the promoting effects of the rhenium. It is understood that any supported silver-based, alkali metal promoted ethylene oxide catalyst which contains other cations and/or anions or any other activators, promoters, enhancers, stabilizers or other catalyst improvers and which contains an amount of rhenium which provides a promoting effect, more preferably which provides higher ethylene oxidation selectivities to ethylene oxide at a given oxygen conversion level and most preferably which provides higher initial ethylene oxidation selectivities than is obtained under the same reaction conditions with the same catalyst not containing a promoting amount of rhenium will fall within the scope of the instant invention and claims.

The rhenium compounds, salts and/or complexes used in the preparation of the instant catalysts are rhenium compounds, salts, and/or complexes that can be solublized in an appropriate solvent. Preferably the solvent is a water-containing solvent. More preferably the solvent is the same solvent used to deposit the silver and the alkali metal promoter. Examples of rhenium compounds include the rhenium salts such as rhenium halides, the rhenium oxyhalides, the rhenates, the perrhenates, the oxides and the acids of rhenium. A preferred compound to be utilized in the impregnation solution is the perrhenate, preferably ammonium perrhenate. However, the alkali metal perrhenates, alkaline earth metal perrhenates, silver perrhenate, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification rhenium heptoxide can be considered to be a perrhenate, i.e., $ReO^-_4$. It is also understood that there are many rhenium compounds that are not soluble per se in water. However, these compounds can be solubilized by utilizing various acids, bases, peroxides, alcohols, etc. After solubilization these compounds could be used, for example, with an appropriate amount of water or other suitable solvent to impregnate the carrier. Of course, it is also understood that upon solubilization of many of these compounds, the original compound no longer exists after solubilization. For example, rhenium metal is not soluble in water. However, it is soluble in concentrated nitric acid as well as in hydrogen peroxide solution. Thus, by using an appropriate reactive solvent one could use rhenium metal to prepare a solubilized rhenium-containing impregnating solution.

A presently preferred aspect of the instant invention is that the rhenium present on the catalyst is present in a form that is extractable in a dilute aqueous base solution. For the purposes of this specification a 20 millimolar aqueous sodium hydroxide solution was chosen as the standard solution to be used to test the extractability of rhenium on the catalyst. It will be clear to one skilled in the art that other concentrations of sodium hydroxide as well as other bases can be utilized to test the extractability of rhenium. Thus, one skilled in the art can utilize other bases, for example, other alkali metal hydroxides, other alkaline earth metal hydroxides, ammonium hydroxide, organic bases, etc., suitably dissolved in an appropriate solvent to extract rhenium and by comparing it with the 20 millimolar aqueous sodium hydroxide solution used herein can determine whether rhenium extractability with other base solutions will be equivalent to the rhenium extractability with the 20 millimolar sodium hydroxide solution.

In the above-noted presently preferred embodiment, the rhenium is not present in the free metallic state, but rather is present as a compound, complex or ion. In a particularly preferred embodiment, the rhenium on the catalyst is in a form that is extractable by dilute basic solution, and particularly with the 20 millimolar dilute sodium hydroxide solution disclosed herein. The base extraction technique can be used on a fresh catalyst, i.e., a catalyst that has gone through all the appropriate preparative techniques and is ready to be placed in an ethylene oxide reactor, or on a used catalyst, i.e., a catalyst that has been used for the production of ethylene oxide and then removed from the reactor. In a typical test procedure utilized herein a 1 to 10 g sample of fresh or reactor-tested catalyst is extracted with 10 to 50 milliters of the 20 millimolar aqueous sodium hydroxide solution at 100° C. for 10 minutes. The amount of rhenium in an aliquot of the cooled extract is determined spectrophotometrically following the procedure of V. W. Meloche et al., *Analytical Chemistry*, 29, 527 (1957). In this procedure, a colored rhenium complex with alpha-furildioxime is formed by reduction of the rhenium species with tin (II) chloride in a dilute hydrochloric acid solution containing a large excess of alpha-furildioxime.

Generally, the carrier is contacted with a silver salt, a silver compound, or a silver complex which has been dissolved in an aqueous solution, so that the carrier is impregnated with said aqueous solution, thereafter the impregnated carrier is separated from the aqueous solution, e.g., by centrifugation or filtration and then dried. The thus obtained impregnated carrier is heated to reduce the silver to metallic silver. It is conveniently heated to a temperature in the range from 50° C. to 600° C., during a period sufficient to cause reduction of the silver salt, complex or compound to metallic silver and to form a layer of finely divided silver, which is bound to the surface of the carrier, both the exterior and pore surface. Air, or other oxygen containing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkylenediamines and ammonia.

One such example of a solution of silver salts comprises an impregnating solution comprising:

A. a silver salt of a carboxylic acid,

B. an organic amine alkaline solubilizing/reducing agent,

C. an aqueous solvent.

Suitable carboxylic acid silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver solubilizing/reducing agents include lower alkylenediamines of from 1 to 5 carbon atoms, mixtures of a lower alkylenediamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are particularly useful. They are the following:

A. vicinal alkylenediamines of from 2 to 4 carbon atoms;

B. mixtures of (1) vicinal alkanolamines of from 2 to 4 carbon atoms and (2) vicinal alkylenediamines of from 2 to 4 carbon atoms;

C. mixtures of vicinal alkylenediamines of from 2 to 4 carbon atoms and ammonia; and D. mixtures of vicinal alkanolamines of from 2 to 4 carbon atoms and ammonia. These solubilizing/reducing agents are generally added in the amount of from 0.1 to 10 moles per mole of silver present.

Particularly preferred solubilizing/reducing agents are:

A. ethylenediamine,

B. ethylenediamine in combination with ethanolamine,

C. ethylenediamine in combination with ammonia, and

D. ethanolamine in combination with ammonia.

Ethylenediamine is most preferred. Ethylenediamine in combination with ethanolamine gives comparable results, but it is believed that impurities that are present in certain commercially available ethanolamine preparations can produce inconsistent results.

When ethylenediamine is used as the sole solubilizing/reducing agent, it is necessary to add amounts of the amine in the range of from 0.1 to 5.0 moles of ethylenediamine per mole of silver.

When ethylenediamine and ethanolamine together are used as the solubilizing/reducing agent, it is suitable to employ from 0.1 to 3.0 moles of ethylenediamine per mole of silver and from 0.1 to 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver-containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115 issued Mar. 1, 1977; U.S. Pat. No. 4,356,312, issued Oct. 26, 1982; U.S. Pat. No. 3,962,136, issued June 8, 1976 and U.S. Pat. No. 4,012,425, issued Mar. 15, 1977 all incorporated by reference herein.

The preferred amount of alkali metal promoter deposited on or present on the surface of the carrier or catalyst generally lies between about 10 and about 3000, preferably between about 15 and about 2000 and more preferably between about 20 and about 1500 ppm by weight of alkali metal calculated on the total catalyst material. Amounts between about 50 and about 1000 ppm are most preferable. Suitable compounds of alkali metal are, for example, the nitrates, carbonates, bicarbonates, oxalates, carboxylic acid salts or hydroxides put in solution, preferably aqueous solution. The more preferred promoters among the alkali metals are the alkali metals comprising the higher alkali metals comprising potassium, rubidium, cesium or mixtures thereof in a promoting amount with the even more preferred promoters being rubidium and/or cesium. Preferably the amount ranges from about 10 and about 3000, more preferably between about 15 and about 2000, even more preferably between about 20 and about 1500 ppm by weight, and most preferably between about 50 and 1000 ppm by weight. The most preferred promoter is cesium, preferably applied as an aqueous solution having cesium nitrate or cesium hydroxide dissolved therein. While the higher alkali metals provide the most significant effect when considering the selectivity, particularly the initial selectivity, it is considered within the scope of the instant preferred embodiment that lithium and/or sodium may also be present in addition to the higher alkali metal(s) in order to provide enhanced or different effects. Thus, the use of Markush terminology in this specification and claims to indicate the higher alkali metals cesium and/or rubidium and/or potassium is not meant and does not exclude the presence, inclusion or the use of lithium and/or sodium in addition to the higher alkali metals. Thus, the use of a Markush recitation in the instant specification and claims means that the elements in the recitation are included, but others are not excluded, i.e., the Markush recitation is an open ended recitation.

There are known excellent methods of applying the promoters coincidentally with the silver on the carrier. Suitable alkali metal salts are generally those which are soluble in the silver-impregnating liquid phase. Besides the above-mentioned compounds may be mentioned the nitrites; the halides, such as fluorides, chlorides, iodides, bromides; oxyhalides; bicarbonates; borates; sulfates; sulfites; bisulfates; acetates; tartrates; lactates and isopropoxides, etc. The use of rhenium or alkali metal salts which have ions which react with the silver ions in solution is preferably avoided, e.g. the use of cesium chloride together with silver nitrate in an aqueous solution, since then some silver chloride is prematurely precipitated. Here the use of cesium nitrate is recommended instead of cesium chloride, for example. However, cesium chloride may be used together with a silver salt-amine-complex in aqueous solution, since then the silver chloride is not precipitated prematurely from the solution.

The promoters may be deposited on the carrier (support) or on the catalyst depending upon the particular impregnation technique or sequence utilized. As used in this specification and claims, the term "on the catalyst" when referring to the deposition or presence of promoters and/or co-promoters refers to the catalyst which comprises the combination of carrier (support) and silver. Thus, the promoters, i.e., alkali metal and rhenium may be found individually or in a mixture thereof on the catalyst, on the support or on both the catalyst and the support. There may be, for example, alkali and rhenium on the catalyst; alkali and rhenium on the support; alkali on the support and rhenium on the catalyst; alkali on the support and a mixture of alkali and rhenium on the catalyst; rhenium on the support and a mixture of alkali and rhenium on the catalyst; rhenium on the support and alkali on the catalyst; a mixture of alkali and rhenium on the support and a mixture of alkali and rhenium on the catalyst; a mixture of alkali and rhenium on the support and alkali on the catalyst; and a mixture of alkali and rhenium on the support and rhenium on the catalyst.

The amount of the alkali metal and/or rhenium promoters on the porous carrier or catalyst may also be regulated within certain limits by washing out the surplus of promoter material with an appropriate solvent, for example, methanol or ethanol.

A particularly preferred process of impregnating the carrier consists of impregnating the carrier with an aqueous solution containing a silver salt of a carboxylic acid, an organic amine, a salt of cesium and ammonium perrhenate dissolved therein. Silver oxalate is a preferred silver salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound and ammonium perrhenate. While addition of the amine to the silver oxide before adding the oxalic acid is possible, it is not preferred since it can give rise to solutions which are unstable or even explosive in nature. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water and ammonium perrhenate is added. Rubidium-, potassium-, sodium-, lithium- and mixtures of alkali metal-containing solutions may be prepared also in these ways. The impregnated carriers are then heated to a temperature between 50° C. and 600° C., preferably between 75° C. and 400° C. to evaporate the liquid and produce a metallic silver.

In general terms, the impregnation process comprises impregnating the support with one or more solutions comprising silver, alkali metal and rhenium. As used in the instant specification and claims, the terminology "impregnating the support with one or more solutions comprising silver, alkali metal and/or rhenium" and similar or cognate terminology means that the support is impregnated in a single or multiple impregnation, with one solution containing silver, alkali metal and rhenium; in multiple impregnations with two or more solutions containing silver, alkali metal and rhenium in differing amounts; or in multiple impregnations with two or more solutions, wherein each solution contains at least one component selected from silver, alkali metal and rhenium with the proviso that all of the components silver, alkali metal and rhenium will individually be found in at least one of the solutions. The concentration of the silver (measured as the metal) in the silver-containing solution will range from about 1 g/liter up to the solubility limit of silver in the solution, preferably from about 10 g/l up to the solubility limit when a single impregnation is utilized. The concentration of the alkali metal (measured as the metal) will range from about $1 \times 10^{-3}$ g/liter to about 12 g/l when a single impregnation is utilized. The concentration of the rhenium (measured as the metal) will range from about $5 \times 10^{-3}$ g/l to about 20 g/l, preferably from about $50 \times 10^{-3}$ g/l to about 20 g/l when a single impregnation step is utilized. Concentrations selected within the above-noted ranges will depend upon the pore volume of the catalyst, the final amount desired in the final catalyst and whether the impregnation is single or multiple. Appropriate concentrations can readily be determined by routine experimentation.

The amount of silver deposited on the support or present on the support is to be a catalytically effective amount of silver, i.e., an amount that catalyzes the reaction of ethylene and oxygen to produce ethylene oxide. Preferably this amount will range from about 1 to about 30 percent by weight of the total catalyst, more preferably from about 1 to about 25 percent by weight of the total catalyst, and even more preferably from about 5 to about 20 percent by weight of the total catalyst. The upper and lower limit of preferred silver concentrations can be suitably varied, depending upon the particular catalytic properties or effect desired or other variables involved. Possible lower limits of silver are, for example, about 1, 3, 5, 6, 8 and 10 percent by weight of the total catalyst. Possible upper limits of silver are, for example, about 15, 16, 18, 20, 22, 25 and 30 percent by weight of the total catalyst.

The amount of alkali metal deposited on the support or catalyst or present on the support or catalyst is to be a promoting amount. Preferably the amount will range from about 10 to about 3000, more preferably from about 15 to about 2000, even more preferably from about 20 to about 1500 and yet even more preferably from about 50 to about 1000 ppm by weight of the total catalyst, measured as the metal. The upper and lower limits of preferred alkali metal concentrations can be suitably varied depending upon the particular promoting effect desired or other variables involved. Possible lower limits of alkali metals are, for example, about 1, 5, 10, 25, 50, 75, 100, 200 and 300 ppm by weight of the total catalyst, measured in the metal. Possible upper limits of alkali metal are, for example, about 250, 300, 400, 500, 600, 700, 800, 900, 1000, 1250, 1500, 2000, 2500 and 3000 ppm by weight of the total catalyst, measured as the metal.

The amount of rhenium deposited on the support or catalyst or present on the support or catalyst is to be a promoting amount. Preferably the amount will range from about 0.01 to about 15, more preferably from about 0.1 to about 10, even more preferably from about 0.2 to about 5 and yet even more preferably from about 0.5 to about 4 $\mu$moles/g of total catalyst, measured as the metal. The upper and lower limits of preferred rhenium concentrations can be suitably varied depending upon the particular promoting effect desired or other variables involved. Possible lower limits of rhenium are, for example, about 0.01, 0.1, 0.2, 0.25, 0.3, 0.4, 0.5, 0.6, 0.7, 0.8, 0.9, 1 and 1.5 $\mu$moles/g of total catalyst. Possible upper limits of rhenium are, for example, about 2.5, 3, 4, 5, 6, 7, 8, 9, 10, 12, 14, 15 and 16 $\mu$moles/g of total catalyst.

It is observed that independent of the form in which the silver is present in the solution before precipitation on the carrier, the term "reduction to metallic silver" is used, while in the meantime often decomposition by heating occurs. It is preferred to use the term "reduction", since the positively charged $Ag^+$ ion is converted into metallic Ag atom. Reduction times may generally vary from about 0.5 minute to about 8 hours, depending on the circumstances.

The silver catalysts according to the present invention have been shown to have a particularly high initial selectivity for ethylene oxide in the direct oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydrocarbons, presence of moderating agents to control the catalytic action, for example, 1-2-dichloroethane, vinyl chloride or chlorinated polyphenyl compounds, the desirability of employing recycle operations or applying successive conversions in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective. For purposes of illustration only, the following table shows the range of conditions that are often used in current commercial ethylene oxide reactor units.

TABLE 2

| *GHSV | 1500–10,000 |
|---|---|
| Inlet pressure | 150–400 psig |
| Inlet Feed | |
| ethylene | 1–40% |
| $O_2$ | 3–12% |
| $CO_2$ | 2–40% |
| ethane | 0–3% |
| Argon and/or methane and/or nitrogen diluent | |
| chlorohydrocarbon moderator 0.3–20 ppmv total | |
| Coolant temperature | 180–315° C. |
| Catalyst temperature | 180–325° C. |
| $O_2$ conversion level | 10–60% |
| EO Production (Work Rate) | 2–16 lbs. EO/cu. ft. catalyst/hr. |

*Liters of gas at standard temperature and pressure passing over the one liter of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200° C. to about 325° C.

The invention will be illustrated by the following illustrative embodiments which are provided for illustration only and are not intended to limit the scope of the instant invention.

ILLUSTRATIVE EMBODIMENTS

Illustrative Embodiment 1

The following illustrative embodiment describes typical preparative techniques for making the catalysts of the instant invention (and comparative catalysts) and the typical technique for measuring the properties of these catalysts.

Part A: Preparation of stock silver oxalate/ethylenediamine solution for use in catalyst preparation (1) Dissolve 415 g reagent-grade NaOH in 2340 ml deionized water. Adjust temperature to 50° C.

(2) Dissolve 1699 g "spectropure" (high-purity) $AgNO_3$ in 2100 ml deionized water. Adjust temperature to 50° C.

(3) Add NaOH solution slowly to $AgNO_3$ solution with stirring, maintaining temperature at 50° C. Stir for 15 minutes after addition is complete, then lower temperature to 40° C.

(4) Insert clean filter wands and withdraw as much water as possible from the precipitate created in step (3) in order remove sodium and nitrate ions. Measure the conductivity of the water removed and add back as much fresh deionized water as was removed by the filter wands. Stir for 15 minutes at 40° C. Repeat this process until the conductivity of the water removed is less than 90 $\mu$mho/cm. Then add back 1500 ml deionized water.

(5) Add 630 g of high-purity oxalic acid dihydrate in approximately 100 g increments. Keep the temperature at 40° C. and stir to mix thoroughly. Add the last portion of oxalic acid dihydrate slowly and monitor pH to ensure that pH does not drop below 7.8. Aim for a pH endpoint of 8.0–8.4. Add high-purity silver oxide if necessary to achieve this endpoint.

(6) Remove as much water from the mixture as possible using clean filter wands in order to form a highly concentrated silver-containing slurry. Cool the silver oxalate slurry to 30° C.

(7) Add 699 g of 92% w ethylenediamine (8% deionized water). Do not allow the temperature to exceed 30° C. during addition.

The above procedure yields a solution containing approximately 27–33% w Ag.

Part B: Catalyst Impregnation Procedures

Catalyst support Example B described in Table 1 is a preferred support for the instant invention and is used in the following examples and illustrative embodiments.

Preparation of undoped impregnating solution is as follows: The stock Ag oxalate/ethylenediamine solution of Part A is diluted preferably with deionized water, or alternatively may be diluted with monoethanolamine, or a mixture of deionized water and monoethanolamine to achieve a Ag concentration of approximately 27.6% by weight. The use of monoethanolamine or monoethanolamine plus water to dilute the stock solution is believed to provide catalysts comparable to those obtained by the use of water. However, it is believed that certain impurities present in monoethanolamine can cause inconsistent results in the catalysts made with monoethanolamine. Hence, water is preferred and was used for all of the examples provided herein.

Preparation of doped impregnation solution is as follows:

For catalyst A (Cs only): Add 46.4 mg of aqueous CsOH solution (50.7% w Cs) directly to 50 g of undoped impregnating solution.

For catalyst B (Cs-Re): Dissolve 55.0 mg of $NH_4ReO_4$ in a minimum volume of 50/50 (w/w) ethylenediamine/deionized water and add to 50 g of undoped impregnation solution. Then add 84.7 mg of aqueous CsOH solution (50.7% w Cs) to the same impregnating solution.

The aqueous cesium hydroxide solution used for catalyst preparation in this and the following illustrative embodiments was doped with a radioactive isotope of cesium ($^{134}Cs$) so that the cesium levels on the finished catalysts could be readily determined by radiotracer analysis. (Alternatively, the levels of cesium and other alkali promoters on finished catalysts can be determined by the water leaching method described below.) The concentration of cesium in this aqueous, radiolabeled cesium hydroxide solution was determined to be 50.7% w by neutron activation analysis at the Nuclear Science Center, Texas A&M University, College Station, Texas, using a TRIGA reactor, an Ortec high-purity Germanium Model BA-GEM-25185 detector, and a Tracor Northern Model 4000 multichannel analyzer. All target and actual cesium levels reported for catalysts in this and the following illustrative embodiments are based upon a value of 50.7% w for the concentration of cesium in the stock, radiolabeled cesium hydroxide solution. However, when this same cesium hydroxide solution was subsequently analyzed by inductively coupled plasma jet-mass spectrometry using a SCIEX Elan 250 instrument, the cesium concentration was found to be 45% w. If this latter value for the cesium concentration in this solution is closer to the actual value, then the absolute levels of cesium for the catalysts described in this and the following illustrative embodiments would be approximately 11.2% lower than those reported.

Part C: Catalyst impregnation and curing

Approximately 30 g of carrier B are placed under 25 mm vacuum for 3 minutes at room temperature. Approximately 50 g of doped impregnating solution is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft./hr. air stream flowing across a cross-sectional area of approximately 3-5 square inches at 250° C. for 5 minutes. If significant monoethanolamine is present in the impregnating solution, then the impregnated carrier is cured by being continuously shaken in a 300 cu. ft./hr. air stream at 250° C. for 2.5 minutes, followed by a 100 cu. ft./hr. air stream at 270° C. for 7.5 minutes (all over a cross-sectional area of approximately 3-5 square inches). The cured catalyst is then ready for testing.

This procedure will yield catalysts on this carrier containing approximately 13.5% w Ag with the following approximate dopant levels and which are approximately optimum in cesium for the given silver and rhenium levels and support with regard to initial selectivity under the test conditions described below.

| catalyst | Cs, ppmw | Re, ppmw |
|---|---|---|
| A | 230 | 0 |
| B | 420 | 372 |

The actual silver content of the catalyst can be determined by any of a number of standard, published procedures. The actual level of rhenium on the catalysts prepared by the above process can be determined by extraction with 20 mM aqueous sodium hydroxide solution, followed by spectrophotometric determination of the rhenium in the extract, as described above. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure 3 to 5 g of crushed catalyst (14-20 mesh) are loaded into a ¼ inch diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 3300 cc of gas per cc of catalyst per hour. The inlet gas pressure is 210 psig.

The gas mixture passed through the catalyst bed (in once-through operation) during the entire test run (including startup) consists of 30% ethylene, 8.5% oxygen, 7% carbon dioxide, 54.5% nitrogen, and 4.4 to 5.6 ppmv vinyl chloride.

The initial reactor (heat medium) temperature is 180° C. After 1 hour at this initial temperature, the temperature is increased to 190° C. for 1 hour, followed by 200° C. (1 hour), 210° C. (1 hour), 220° C. (1 hour), 227° C. (2 hours), and 235° C. (2 hours), and 242° C. (2 hours). The temperature is then adjusted so as to achieve a constant oxygen conversion level of 40%. Performance data at this conversion level are usually obtained when the catalyst has been onstream for a total of 16±4 hours and are referred to as "initial performance data" in the examples given below. Due to slight differences in feed gas composition, gas flow rates, and the calibration of analytical instruments used to determine the feed and product gas compositions, the measured selectivity and activity of a given catalyst may vary slightly from one test run to the next. To allow meaningful comparison of the preformances of catalysts tested at different times, all catalysts described in this and the following illustrative embodiments were tested simultaneously with a standard catalyst having the composition of catalyst A or with a different catalyst which has been standardized with reference to catalyst A. All performance data reported in this and the following illustrative embodiments are corrected and stated relative to the average initial performance of catalyst A ($S_{40}=80.0\%$; $T_{40}=242°$ C.).

Typical initial performances at 40% $O_2$ conversion for the above recipe are as follows:

| catalyst | selectivity | | temperature | |
|---|---|---|---|---|
| A | = | 80.0% | = | 242° C. |
| B | | 81.9% | | 248° C. |

Illustrative Embodiment 2

Using the general preparative technique of Illustrative Embodiment 1, a series of catalysts were prepared utilizing carrier B described in Table 1. The catalysts were prepared without using monoethanolamine. One series of catalysts contained 2 mmol (millimoles) of rhenium per kilogram of catalyst and the other series of catalysts was made in the identical fashion except that they contained no rhenium. In both series the concentration of cesium in the individual catalysts was varied. The catalysts were tested as described in Illustrative Embodiment 1 and the results are shown in Table 3. The cesium levels reported in Table 3 were obtained by the radiotracer analysis technique described in Illustrative Embodiment 1, assuming a concentration of 50.7%w cesium for the radiolabeled, aqueous cesium hydroxide solution used in catalyst preparation. Further, the results from these tests in the form of the initial selectivity versus cesium concentration are plotted in FIG. 1. In this Figure one can see the beneficial effects of rhenium which are indicated by the highlighted area between the two curves to the right of their cross-over point. It can be seen from FIG. 1 that the use of rhenium provides not only an increase in the absolute value of the initial selectivity obtained at optimum cesium concentration, but also a significantly improved initial selectivity of the catalyst at high cesium concentrations e.g., 300 ppm cesium and over.

Illustrative Embodiment 3

A series of catalysts were prepared in a fashion similar to the technique described in Illustrative Embodiment 1 using different carriers having those properties described in Table 1 in the specification. The catalysts were made without monethanolamine. The catalysts were tested as described in Illustrative Embodiment 1 and the results are shown below in Table 4. Unless otherwise noted, all catalysts listed in Table 4 have cesium levels which give the optimum (highest) initial selectivity obtained under these test conditions for a catalyst made on the indicated carrier with the indicated levels of silver and rhenium. The cesium levels reported in Table 4 were obtained by the radiotracer analysis technique described in Illustrative Embodiment 1, assuming a concentration of 50.7% w cesium for the radiolabeled, aqueous cesium hydroxide solution used in catalyst preparation. Catalyst 4–6 was not made using the identical support of catalyst 4–5 but rather used a comparable support from a different lot which had a surface area of 0.44 m$^2$/g, a water pore volume of 0.42 cc/g, a water-leachable sodium content approximately 50% higher and an acid-leachable sodium content approximately 100% higher. (This support is referred to hereinafter as C').

Illustrative Embodiment 4

A series of catalysts were prepared on carrier Example B of Table 1 in a fashion similar to that described in Illustrative Embodiment 1 but utilizing different rhenium concentrations. The catalysts were made without monethanolamine. The catalysts were tested as described in Illustrative Embodiment 1 and the results are shown in Table 5 below. Unless otherwise noted, all catalysts listed in Table 5 have cesium levels which give the optimum (highest) initial selectivity obtained under these test conditions for a catalyst made on this support with the indicated levels of silver and rhenium. The cesium levels reported in Table 5 were obtained by the radiotracer analysis technique described in Illustrative Embodiment 1, assuming a concentration of 50.7% w cesium for the radiolabeled, aqueous cesium hydroxide solution used in catalyst preparation.

Illustrative Embodiment 5

A series of catalysts were prepared in a fashion similar to that described in Illustrative Embodiment 1 using support Example B of Table 1. The catalysts were made without monoethanolamine. In this series different alkali metals were utilized as alkali metal hydroxides. The catalysts were tested as described in Illustrative Embodiment 1 and the results are shown in Table 6 below. The alkali levels presented represent target levels. Unless otherwise noted, all catalysts listed in Table 6 have target alkali levels which give the optimum (highest) initial selectivity obtained under these test conditions for a catalyst made with the indicated alkali metal hydroxide on this support with the indicated levels of silver and rhenium. For examples 6–13 and 6–, the target cesium content was fixed at 160 ppm and the rubidium concentration was optimized to provide the highest initial selectivity under these test conditions at the indicated levels of silver and rhenium. Also, for these two examples, the support, which was otherwise comparable to support B, had a surface of 0.45 m$^2$/g instead of 0.42 m$^2$/g and about 10–15% lower levels of leachable sodium (this support is referred to hereinafter as support B').

Illustrative Embodiment 6

Two sets of catalysts were prepared in a fashion similar to that described in Illustrative Embodiment 1 using support Example B of Table 1 with the exception that ammonium molybdate $((NH_4)_6Mo_7O_{24}.4H_2O)$ was added to the impregnation solution in sufficient quantity to provide about 96 ppm by weight of Mo in the final catalyst. The catalysts were made without monoethanolamine. The catalysts contained potassium (target) levels which provide the optimum (highest) initial selectivity under the test conditions described in Illustrative Embodiment 1 at the noted levels of silver, rhenium and molybdenum. Catalyst example 7-1 (prepared using support B') which contained 13.2% w silver, no rhenium, 180 ppm K (target level) and 96 ppm Mo had an initial $S_{40}$ of 77.0% and an initial $T_{40}$ of 261° C. and catalyst example 7-2 which 14.5% w silver, 186 ppm by weight of rhenium (target level), 160 ppm K (target level) and 96 ppm Mo (target level) had an initial $S_{40}$ of 81.1% and an initial $T_{40}$ of 279° C. For comparative purposes, note that catalyst Example 6–7 which contains no rhenium or molybdenum has a $S_{40}$ of 79.4 and a $T_{40}$ of 240° C.

Illustrative Embodiment 7

Two catalysts were prepared in a fashion similar to that described in Illustrative Embodiment 1 using support Example B of Table 1. The catalysts both contained cesium levels which had been optimized to provided the highest initial selectivities under the test conditions described in Illustrative Embodiments 1 . Both catalysts were made without using monoethanolamine.

Catalyst VII-1 was prepared using 2 μmoles/g each of NH$_4$ReO$_4$ and (NH$_4$)$_2$SO$_4$. Catalyst VII-2 was prepared using 2 μmoles/g each of (NH$_4$)ReO$_4$ and Na$_2$SO$_4$. The catalysts were tested as described in Illustrative Embodiment 1 and the results are listed below:

| Catalyst | % w Ag | Cs* ppmw | Na** ppmw | Re** umoles/g | $S_{40}$ | $T_{40}$ |
|---|---|---|---|---|---|---|
| VII-1 | 12.8 | 513 | 0 | 2 | 81.7% | 274° C. |
| VII-2 | 13.5 | 424 | 92 | 2 | 83.9% | 253° C. |

*by radiotracer, assuming a concentration of 50.7% w cesium for the radiolabeled, aqueous cesium hydroxide solution used in catalyst preparation.
**target levels It can be seen from the above results that the catalyst containing the mixture of cesium and sodium as alkali metal promoters is more selective and more active than the catalyst which contains only cesium as the alkali metal promoter.

Illustrative Embodiment 8

Three catalysts were prepared in a fashion similar to that described in Illustrative Embodiment 1 (no monoethanolamine) using support Example B of Table 1. The catalysts contained cesium levels which had been optimized to provide the highest initial selectivities under the test conditions described in Illustrative Embodiment 1. Catalyst VIII-1 was prepared using one μmole/g of NH₄ReO₄ and two μmoles/g of (NH₄)₂SO₄. Catalyst VIII-2 was prepared using one μmole/g of NH₄ReO₄ and two μmoles/g of Li₂SO₄. Catalyst VIII-3 was prepared using one μmole/g of NH₄ReO₄ and two μmoles/g of Na₂SO₄. The catalysts were tested as described in Illustrative Embodiment 1 and the results are listed below:

| Catalyst | % w Ag | Cs* ppmw | Li* ppmw | Na* ppmw | Re μmoles/g | S$_{40}$ | T$_{40}$ |
|---|---|---|---|---|---|---|---|
| VIII-1 | 13.8 | 505 | 0 | 0 | 1 | 82.0% | 273° C. |
| VIII-2 | 13.9 | 398 | 28 | 0 | 1 | 83.1% | 249° C. |
| VIII-3 | 14.8 | 411 | 0 | 92 | 1 | 80.9% | 248° C. |

*by radiotracer, assuming a concentration of 50.7% w cesium for the radiolabeled, aqueous cesium hyroxide solution used in catalyst preparation.
**target levels It can be seen from the above results that Catalyst VIII-2 containing a mixture of cesium plus lithium as the alkali promoters is more selective and more active than the catalyst with only cesium as the alkali promoter. At this level of rhenium (half of that of Illustrative Embodiment 7), Catalyst VIII-3 containing both cesium plus sodium as alkali promoters shows improved activity over the comparable catalyst containing only cesium as alkali promoter whereas the selectivity is diminished.

TABLE 3
CS OPTIMIZATION FOR CATALYSTS WITH AND WITHOUT RE

| Experiment No. | % wAg | Re Target Level, ppmw | Cs, ppmw (Radiotracer Analysis) | Initial S$_{40}$, % | Initial T$_{40}$, °C. |
|---|---|---|---|---|---|
| 3-1** | 13.6 | 0 | 0 | 74.6 | 229 |
| 3-2** | 13.6 | 0 | 104 | 77.6 | 232 |
| 3-3 | 14.3 | 0 | 236 | 80.0 | 242 |
| 3-4 | 14.3 | 0 | 301 | 79.4 | 243 |
| 3-5** | 13.6 | 0 | 416 | 77.0 | 259 |
| 3-6 | 14.3 | 372* | 0 | 54.3 | 236 |
| 3-7 | 14.3 | 372 | 110 | 69.9 | 243 |
| 3-8 | 14.3 | 372 | 209 | 75.8 | 239 |
| 3-9 | 14.3 | 372 | 327 | 79.8 | 240 |
| 3-10 | 14.2 | 372 | 403 | 81.8 | 245 |
| 3-11 | 14.2 | 372 | 438 | 81.9 | 248 |
| 3-12 | 14.2 | 372 | 488 | 81.4 | 250 |
| 3-13 | 14.2 | 372 | 512 | 81.0 | 251 |
| 3-14 | 14.2 | 372 | 561 | 80.3 | 256 |

*2.0 μmoles/g
**Performance data obtained at 40% oxygen conversion when catalyst had been onstream for 32 ± 4 hours.

TABLE 4
CESIUM OPTIMIZED CATALYSTS ON DIFFERENT CARRIERS WITH AND WITHOUT RHENIUM

| Experiment No. | Carrier | % wAg | Re Target Level, ppmw | Cs, ppmw (Radiotracer Analysis) | Initial S$_{40}$, % | Initial T$_{40}$, °C. |
|---|---|---|---|---|---|---|
| 4-1 | A | 10.3 | 0 | 162 | 80.1 | 248 |
| 4-2 | A | 10.3 | 186* | 261 | 81.4 | 253 |
| 4-3 | B | 14.3 | 0 | 236 | 80.0 | 242 |
| 4-4 | B | 14.2 | 372** | 438 | 81.9 | 248 |
| 4-5 | C | 14.1 | 0 | 256 | 80.3 | 240 |
| 4-6 | C' | 13.5 | 372 | 469 | 81.4 | 241 |
| 4-7 | D | 15.0 | 0 | 309 | 80.9 | 240 |
| 4-8 | D | 15.1 | 372 | 434 | 82.7 | 249 |

*1.0 μmoles/g
**2.0 μmoles/g

TABLE 5
CS OPTIMIZED CATALYSTS WITH DIFFERENT RE LEVELS

| Experiment No. | % wAg | Re Target Level ppmw (μmoles/g) | Cs, ppmw (Radiotracer Analysis) | Initial S$_{40}$, % | Initial T$_{40}$, °C. |
|---|---|---|---|---|---|
| 5-1 | 14.3 | 0(0) | 236 | 80.0 | 242 |
| 5-2 | 13.8 | 93(0.5) | 297 | 80.4 | 244 |
| 5-3 | 13.9 | 186(1.0) | 360 | 80.6 | 241 |
| 5-4 | 14.2 | 372(2.0) | 438 | 81.9 | 248 |
| 5-5 | 14.5 | 465(2.5) | 486 | 82.3 | 248 |
| 5-6 | 14.1 | 558(3.0) | 567 | 82.5 | 248 |
| 5-7 | 14.0 | 744(4.0) | 634 | 80.2 | 248 |

TABLE 6
OPTIMIZATION WITH DIFFERENT ALKALIS, WITH AND WITHOUT RE

| Experiment No. | % wAg | Alkali Dopant Added | Target ppmw Alkali | Re Target Level, ppmw | Initial S$_{40}$, % | Initial T$_{40}$, °C. |
|---|---|---|---|---|---|---|
| 6-1 | 13.6 | None | 0 | 0 | 74.6 | 229 |
| 6-2 | 14.3 | None | 0 | 372* | 54.3 | 236 |
| 6-3 | 14.3 | Cs | 230 | 0 | 80.0 | 242 |
| 6-4 | 14.2 | Cs | 420 | 372 | 81.9 | 248 |
| 6-5 | 14.0 | Rb | 170 | 0 | 79.4 | 238 |
| 6-6 | 14.6 | Rb | 305 | 372 | 80.0 | 246 |
| 6-7 | 14.6 | K | 130 | 0 | 79.4 | 240 |
| 6-8 | 14.5 | K | 200 | 372 | 78.1 | 239 |
| 6-9 | 14.4 | Na | 207 | 0 | 76.5 | 234 |
| 6-10 | 14.7 | Na | 92 | 372 | 74.3 | 246 |
| 6-11 | 13.9 | Li | 40 | 0 | 74.8 | 233 |
| 6-12 | 14.2 | Li | 120 | 372 | 63.5 | 239 |
| 6-13 | 13.2 | Cs + Rb | 160 + 110 | 0 | 79.4 | 245 |
| 6-14 | 13.2 | Cs + Rb | 160 + 195 | 372 | 81.3 | 256 |

*2.0 μmoles/g

I claim:
1. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of alkali metal and a promoting amount of rhenium supported on a suitable support.

2. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising silver, alkali metal promoter and from about 0.2 to about 5 millimoles of rhenium promoter, measured as the metal, per kilogram of total catalyst, supported on a porous, refractory support; the combination of silver, alkali metal promoter, rhenium promoter and support affording a higher selectivity to ethylene oxide at a given oxygen conversion level than is obtained under the same reaction conditions with the same combination of silver and support and none or one of the promoters selected from rhenium and alkali metal.

3. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, alkali metal promoter and from about 0.2 to about 5 millimoles of rhenium, measured as the metal, per kilogram of total catalyst supported on a porous, refractory support wherein the rhenium is applied to the support in the form of a perrhenate or rhenium heptoxide; the combination of silver, alkali metal promoter, rhenium and support affording a higher selectivity to ethylene oxide at a given oxygen conversion level than is obtained under the same reaction conditions with the same combination of silver and support and none or one of the promoters selected from rhenium and alkali metal.

4. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, alkali metal promoter and from about 0.2 to about 5 millimoles of rhenium, measured as the metal, per kilogram of total catalyst in a form which is extractable in a dilute (20 millimolar) aqueous solution of sodium hydroxide, supported on a porous, refractory support; the combination of silver, alkali metal promoter, rhenium and support affording a higher selectively to ethylene oxide at a given oxygen conversion level than is obtained under the same reaction conditions with the same combination of silver and support and none or one of the promoters selected from rhenium and alkali metal.

5. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, alkali metal promoter and from about 0.2 to about 5 millimoles of rhenium, measured as the metal, per kilogram of total catalyst in a form which is extractable in a dilute (20 millimolar) aqueous solution of sodium hydroxide supported on a porous, refractory support wherein the rhenium is applied to the support in the form of a perrhenate or rhenium heptoxide; the combination of silver, alkali metal promoter, rhenium and support affording a higher selectivity to ethylene oxide at a given oxygen conversion level than is obtained under the same reaction conditions with the same combination of silver and support and none or one of the promoters selected from rhenium and alkali metal.

6. The process of claims 1, 2, 3, 4 or 5 wherein in the catalyst the support comprises alpha alumina.

7. The process of claim 6 wherein in the catalyst the alpha alumina has a surface area ranging from about 0.05 to about 5 m²/g.

8. The process of claim 7 wherein in the catalyst the support surface area ranges from about 0.1 to about 3 m²/g.

9. The process of claim 8 wherein in the catalyst the silver ranges from about 1 to about 25 percent by weight of the total catalyst, and the alkali metal promoter ranges from about 20 to about 1500 parts by weight, measured as the metal, per million parts by weight of the total catalyst.

10. The process of claim 9 wherein in the catalyst the silver ranges from about 5 to about 20 percent by weight of the total catalyst and the alkali metal promoter ranges from about 50 to about 1000 parts by weight, measured as the metal, per million parts by weight of the total catalyst.

11. The process of claim 10 wherein in the catalyst the alkali metal and rhenium are found on the surface of the support or on the surface of the catalyst.

12. The process of claim 10 wherein in the catalyst the alkali metal and rhenium are found individually or in a mixture thereof on the catalyst, on the support or on both the catalyst and the support.

13. The process of claim 10 wherein the selectivity is measured at an oxygen conversion level of about 40% at a gas hourly space velocity of about 3300 and when the catalyst has been placed on stream for about 16±4 hours.

14. The process of claim 1 wherein in the catalyst said promoting amount of alkali metal and rhenium is such as to provide a higher selectivity to ethylene oxide at a given oxygen conversion level under a given set of reaction conditions for the catalyst than for a comparable catalyst without alkali metal and/or rhenium.

15. The process of claim 14 wherein the selectivity is measured at an oxygen conversion level of about 40% at a gas hourly space velocity of about 3300 and when the catalyst has been placed onstream for about 16±4 hours.

16. The process of claim 1 wherein in the catalyst the silver ranges from about 1 to about 25 percent by weight of the total catalyst, the alkali metal promoter ranges from about 20 to about 1500 parts by weight, measured as the metal, per million parts by weight of total catalyst and the rhenium ranges from about 0.2 to about 5 millimoles of rhenium, measured as the metal, per kilogram of total catalyst.

17. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of a higher alkali metal comprising potassium, rubidium, cesium, or mixtures thereof and a promoting amount of rhenium supported on a suitable support.

18. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising a catalytically effective amount of silver, a promoting amount of a higher alkali metal selected from the group consisting of potassium, rubidium, cesium and mixtures thereof and a promoting amount of rhenium supported on a porous, refractory support.

19. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof and from about 0.2 to about 5 millimoles of rhenium promoter measured as the metal, per kilogram of total catalyst supported on a porous, refractory support; the combination of silver, higher alkali metal promoter, rhenium promoter and support affording a higher selectivity to ethylene oxide at a given oxygen conversion level than is obtained under the same reaction conditions with the same combination of silver and support and none or one of the promoters selected from rhenium and higher alkali metal.

20. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof and from about 0.2 to about 5 millimoles of rhenium, measured as the metal, per kilogram of total catalyst supported on a porous, refractory support wherein the rhenium is applied to the support in the form of a perrhenate or rhenium heptoxide; the combination of silver, higher alkali metal promoter, rhenium and support affording a higher selectivity to ethylene oxide at a given oxygen conversion level than is obtained under the same reaction conditions with the same combination of silver and support and none or one of the promoters selected from rhenium and higher alkali metal.

21. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof and from about 0.2 to about 5 millimoles of rhenium, measured as the metal, per kilogram of total catalyst in a form which is extractable in a dilute (20 millimolar) aqueous solution of sodium hydroxide, supported on a porous, refractory support; the combination of silver, higher alkali metal promoter, rhenium and support affording a higher selectivity to ethylene oxide at a given oxygen conversion level than is obtained under the same reaction conditions with the same combination of silver and support and none or one of the promoters selected from rhenium and higher alkali metal.

22. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising silver, a higher alkali metal promoter comprising potassium, rubidium, cesium or mixtures thereof and from about 0.2 to about 5 millimoles of rhenium, measured as the metal, per kilogram of total catalyst in a form which is extractable in a dilute (20 millimolar) aqueous solution of sodium hydroxide, supported on a porous, refractory support wherein the rhenium is applied to the support in the form of a perrhenate or rhenium heptoxide; the combination of silver, higher alkali metal promoter, rhenium and support affording a higher selectivity to ethylene oxide at a given oxygen conversion level than is obtained under the same reaction conditions with the same combination of silver and support and none or one of the promoters selected from rhenium and higher alkali metal.

23. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof and from about 0.2 to about 5 millimoles of rhenium, measured as the metal, per kilogram of total catalyst supported on a porous, refractory support comprising alpha alumina having a surface area ranging from about 0.1 to about 3 $m^2/g$ and a water pore volume ranging from about 0.25 to about 0.55 cc/gm; the combination of silver, higher alkali metal, rhenium and support affording a higher selectivity to ethylene oxide at a given oxygen conversion level than is obtained under the same reaction conditions with the same combination of silver and support and none or one of the promoters selected from rhenium and higher alkali metal.

24. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof and from about 0.2 to about 5 millimoles of rhenium, measured as the metal, per kilogram of total catalyst supported on a porous, refractory support comprising alpha alumina having a surface area ranging from about 0.1 to about 3 $m^2/g$ and a water pore volume ranging from about 0.25 to about 0.55 cc/gm wherein the rhenium is applied to support in the form of a perrhenate or rhenium heptoxide; the combination of silver, higher alkali metal promoter, rhenium and support affording a higher selectivity to ethylene oxide at a given oxygen conversion level than is obtained under the same reaction conditions with the same combination of silver and support and none or one of the promoters selected from rhenium and higher alkali metal.

25. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof and from about 0.2 to about 5 millimoles of rhenium, measured as the metal, per kilogram of total catalyst in a form which is extractable in a dilute (20 millimolar) aqueous solution of sodium hydroxide supported on a porous, refractory support comprising alpha alumina having a surface area ranging from about 0.1 to about 3 $m^2/g$ and a water pore volume ranging from about 0.25 to about 0.55 cc/gm; the combination of silver, higher alkali metal, rhenium and support affording a higher selectivity to ethylene oxide at a given oxygen conversion level than is obtained under the same reaction conditions with the same combination of silver and support and none or one of the promoters selected from rhenium and higher alkali metal.

26. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of a higher alkali metal promoter selected from potassium, rubidium, cesium and mixtures thereof and from about 0.2 to about 5 millimoles of rhenium, measured as the metal, per kilogram of total catalyst in a form which is extractable in a dilute (20 millimolar) aqueous solution of sodium hydroxide supported on a porous, refractory support comprising alpha alumina having a surface area ranging from about 0.1 to about 3 $m^2/g$ and a water pore volume ranging from about 0.25 to about 0.55 cc/g wherein the rhenium is applied to the support in the form of a perrhenate or rhenium heptoxide; the combination of silver, higher alkali metal, rhenium and support affording a higher selectivity to ethylene oxide at a given oxygen conversion level than is obtained under the same reaction conditions with the same combination of silver and support and none or one of the promoters selected from rhenium and higher alkali metal.

27. The process of claims 17, 18, 19, 20, 21 or 22 wherein in the catalyst the support comprises alpha alumina.

28. The process of claims 17, 18, 19, 20, 21 or 22 wherein in the catalyst the support comprises alpha alumina which has a surface area ranging from about 0.05 to about 5 $m^2/g$ and a water pore volume ranging from about 0.10 to about 0.75 cc/g.

29. The process of claim 28 wherein the support surface area ranges from about 0.1 to about 3 $m^2/g$.

30. The process of claims 17 or 18 wherein in the catalyst the silver ranges from about 1 to about 25 percent by weight of the total catalyst, the higher alkali metal promoter ranges from about 20 to about 1500 parts by weight, measured as the metal, per million parts by weight of total catalyst, the rhenium ranges from about 0.2 to about 5 millimoles of rhenium, measured as the metal, per kilogram of total catalyst and the support comprises alpha alumina with a surface area ranging from about 0.05 to about 5 $m^2/g$.

31. The process of claim 30 wherein in the catalyst said promoting amount of alkali metal and rhenium is such as to provide a higher selectivity to ethylene oxide at a given oxygen conversion level under a given set of reaction conditions for the catalyst than for a comparable catalyst without alkali metal and/or rhenium.

32. The process of claim 31 wherein the selectivity is measured at an oxygen conversion level of about 40% at a gas hourly spece velocity of about 3300 and when the catalyst has been placed onstream for about 16±4 hours.

33. The catalyst of claim 30 wherein in the catalyst the higher alkali metal ranges from about 50 to about 1000 ppm by weight.

34. The process of claim 33 wherein the higher alkali metal comprises potassium.

35. The process of claim 33 wherein in the catalyst the higher alkali metal comprises rubidium.

36. The process of claim 33 wherein in the catalyst the higher alkali metal comprises cesium.

37. The process of claim 36 wherein in the catalyst the higher alkali metal comprises potassium and cesium.

38. The process of claim 36 wherein in the catalyst the higher alkali metal comprises rubidium and cesium.

39. The process of claim 36 wherein in the catalyst the higher alkali metal comprises cesium, rubidium and potassium.

40. The process of claim 36 wherein in the catalyst the alkali metal and rhenium are found on the surface of the support or on the surface of the catalyst.

41. The process of claim 36 wherein in the catalyst the alkali metal and rhenium are found individually or in a mixture thereof on the catalyst, on the support or on both the catalyst and the support.

42. The process of claims 19, 20, 21 or 22 wherein in the catalyst the silver ranges from about 1 to about 25 percent by weight of the total catalyst and the alkali metal promoter ranges from about 20 to about 1500 parts by weight, measured as the metal, per million parts by weight of the total catalyst.

43. The process of claim 42 wherein in the catalyst the silver ranges from about 5 to about 20 percent by weight of the total catalyst and the alkali metal promoter ranges from about 50 to about 1000 parts by weight, measured as the metal, per million parts by weight of the total catalyst.

44. The process of claim 43 wherein in the catalyst the alkali metal comprises potassium.

45. The process of claim 43 wherein in the catalyst the alkali metal comprises rubidium.

46. The process of claim 43 wherein in the catalyst the alkali metal comprises cesium.

47. The process of claim 43 wherein in the catalyst the alkali metal and rhenium are found on the surface of the support or on the surface of the catalyst.

48. The process of claim 43 wherein in the catalyst the alkali metal and rhenium are found individually or in a mixture thereof on the catalyst, on the support or on both the catalyst and the support.

49. The process of claim 43 wherein in the catalyst the selectivity is measured at an oxygen conversion level of about 40% at a gas hourly space velocity of about 3300 and when the catalyst has been placed onstream for about 16±4 hours.

50. The process of claims 23, 24, 25 or 26 wherein in the catalyst the silver ranges from about 5 to about 20 percent by weight.

51. The process of claims 23, 24, 25 or 26 wherein in the catalyst the alkali metal and rhenium are found on the surface of the support.

52. The process of claims 23, 24, 25 or 26 wherein in the catalyst the alkali metal and rhenium are found on the surface of the catalyst.

53. The process of claims 23, 24, 25 or 26 wherein in the catalyst the alkali metal and rhenium are found individually or in a mixture thereof on the catalyst, on the support or on both the catalyst and the support.

54. The process of claim 53 wherein the selectivity is measured at an oxygen conversion level of about 40% at a gas hourly space velocity of about 3300 and when the catalyst has been placed onstream for about 16±4 hours.

55. The process of claim 50 wherein in the catalyst the higher alkali metal comprises potassium.

56. The process of claim 50 wherein in the catalyst the higher alkali metal comprises rubidium.

57. The process of claim 50 wherein in the catalyst the higher alkali metal comprises cesium.

58. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst comprising a catalytically effective amount of silver, a promoting amount of cesium and a promoting amount of rhenium on a porous refractory support comprising alpha alumina.

59. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter and from about 0.2 to about 5 millimoles of rhenium, measured as the metal, per kilogram of total catalyst supported on a porous, refractory support comprising alpha alumina having a surface area ranging from about 0.1 to about 3 $m^2/g$ and a water pore volume ranging from about 0.25 to about 0.55 cc/gm; the combination of silver, cesium promoter, rhenium and support affording a higher selectivity to ethylene oxide at a given oxygen conversion level than is obtained under the same reaction conditions with the same combination of silver and support and none or one of the promoters selected from rhenium and cesium.

60. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter and from about 0.2 to about 5 millimoles of rhenium, measured as the metal, per kilogram of total catalyst supported on a porous refractory support comprising alpha alumina having a surface area ranging from about 0.1 to about 3 $m^2/g$ and a water pore volume ranging from about 0.25 to about 0.55 cc/g wherein the rhenium is applied to the support as rhenium heptoxide or ammonium or alkali metal perrhenate or mixtures thereof; the combination of silver, cesium promoter, rhenium and support affording a higher selectivity to ethylene oxide at a given oxygen conversion level than is obtained under the same reaction conditions with the same combination of silver and support and none or one of the promoters selected from rhenium and cesium.

61. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter and from about 0.2 to about 5 millimoles of rhenium, measured as the metal, per kilogram of total catalyst in a form which is extractable in a dilute (20 millimolar) aqueous solution of sodium hydroxide supported on a porous, refractory support comprising alpha alumina having a surface area ranging from about 0.1 to about 3 $m^2/g$ and a water pore volume ranging from about 0.25 to about 0.55 cc/gm; the combination of silver, cesium promoter, rhenium and support affording a higher selectivity to ethylene oxide at a given oxygen conversion level than is obtained under the same reaction conditions with the same combination of silver and support and none or one of the promoters selected from rhenium and cesium.

62. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst comprising from about 1 to about 25 percent by weight of total catalyst of silver, from about 50 to about 1000 parts by weight, measured as the metal, per million parts by weight of total catalyst of cesium promoter and from about 0.2 to about 5 millimoles of rhenium, measured as the metal, per kilogram of total catalyst in a form which is extractable in a dilute (20 millimolar) aqueous solution of sodium hydroxide supported on a porous refractory support comprising alpha alumina having a surface area ranging from about 0.1 to about 3 $m^2/g$ and a water pore volume ranging from about 0.25 to about 0.55 cc/g wherein the rhenium is applied to the support as rhenium heptoxide or ammonium or alkali metal perrhenate or mixtures thereof; the combination of silver, cesium promoter, rhenium and support affording a higher initial selectivity to ethylene oxide at a given oxygen conversion level than is obtained under the same reaction conditions with the same combination of silver and support and none or one of the promoters selected from rhenium and cesium.

63. The process of claim 58 wherein in the catalyst the silver ranges from about 1 to about 25 percent by weight of the total catalyst, the cesium ranges from about 20 to about 1500 parts by weight, measured as the metal, per million parts by weight of the total catalyst and the rhenium ranges from about 0.2 to about 5 millimoles of rhenium, measured as the metal, per kilogram of total catalyst.

64. The process of claim 63 wherein in the catalyst the cesium ranges from about 50 to about 1000 ppm.

65. The process of claim 64 wherein in the catalyst the support has a surface area ranging from about 0.05 to about 5 m²/g.

66. The process of claim 65 wherein in the catalyst the support surface area ranges from about 0.1 to about 3 m²/g.

67. The process of claim 58 wherein in the catalyst said promoting amount of cesium and rhenium is such as to provide a higher selectivity to ethylene oxide at a given oxygen conversion level under a given set of reaction conditions for the catalyst than for a comparable catalyst without cesium and/or rhenium.

68. The process of claims 59, 60, 61, 62 or 67 wherein the selectivity is measured at an oxygen conversion level of about 40% at a gas hourly space velocity of about 3300 and when the catalyst has been placed onstream for about 16±4 hours.

69. The process of claims 58, 59, 60, 61 or 63 wherein in the catalyst the cesium and rhenium are found on the surface of the catalyst.

70. The process of claims 58, 59, 60, 61 or 62 wherein in the catalyst the cesium and rhenium are found on the surface of the support.

71. The process of claims 58, 59, 60, 61 or 62 wherein in the catalyst the cesium and rhenium are found individually or in a mixture thereof on the catalyst, on the support or on both the catalyst and the support.

72. The process of claim 71 wherein the selectivity is measured at an oxygen conversion level of about 40% at a gas hourly space velocity of about 3300 and when the catalyst has been placed onstream for about 16±4 hours.

73. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst which comprises impregnating a porous refractory support with a catalytically effective amount of silver, a promoting amount of alkali metal and a promoting amount of rhenium.

74. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process of which comprises impregnating a porous refractory support with one or more solutions comprising silver, alkali metal and/or rhenium wherein the concentration of the silver (measured as the metal) in the solution ranges from about 1 g/l to the solubility limit of silver in the solution, the concentration of alkali metal (measured as the metal) in the solution ranges from about $1 \times 10^{-3}$ g/l to about 12 g/l and the concentration of the rhenium (measured as the metal) ranges from about $5 \times 10^{-3}$ g/l to about 20 g/l to provide the catalyst with a catalytically effective amount of silver, a promoting amount of alkali metal and a promoting amount of rhenium.

75. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst which comprises using a catalyst prepared by a process which comprises impregnating a porous refractory support with one or more solutions comprising solvent having silver compound(s) dissolved therein, and/or alkali metal compound(s) dissolved therein and/or rhenium-containing compound(s) dissolved therein sufficient to deposit on the support from about 1 to about 25 percent by weight of total catalyst of silver compound(s), measured as the metal, from about 20 to about 1500 ppm by weight of alkali metal compound(s), measured as the metal and from about 0.2 to about 5 millimoles per kilogram of total catalyst, measured as the metal, of rhenium-containing compound(s) to provide the catalyst with a catalytically effective amount of silver, a promoting amount of alkali metal and a promoting amount of rhenium.

76. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support with one or more solutions comprising silver ions, alkali metal ions, rhenium-containing ions or mixtures thereof sufficient to deposit on the carrier from about 1 to about 25 percent by weight of total catalyst of silver, from about 20 to about 1500 parts by weight, measured as the metal, per million parts by weight of total catalyst, of alkali metal compound(s), and from about 0.2 to about 5 millimoles of rhenium-containing compound(s), measured as the metal, per kilogram of total catalyst, and after impregnation, reducing the silver on the support to metallic silver to cause the combination of silver, alkali metal promoter, rhenium and support to have a higher selectivity to ethylene oxide at a given oxygen conversion level than is obtained under the same reaction conditions with the same combination of silver and support and none or one of the promoters selected from rhenium and alkali metal.

77. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support with one or more solutions comprising silver ions, alkali metal ions, rhenium-containing ions or mixtures thereof sufficient to deposit on the support from about 1 to about 25 percent by weight of total catalyst of silver, from about 20 to about 1500 parts by weight, measured as the metal, per million parts by weight of total catalyst, of alkali metal compound(s), and from about 0.2 to about 5 millimoles of rhenium compound(s), measured as the metal, per kilogram of total catalyst, said rhenium compound(s) providing in the final catalyst rhenium in a form which is extractable in a dilute (20 millimolar) aqueous sodium hydroxide solution; and after impregnation, reducing the silver on the support to metallic silver to cause the combination of silver, alkali metal promoter, rhenium and support to have a higher selectivity to ethylene oxide at a given oxygen conversion level than is obtained under the same reaction conditions with the same combination of silver and support and none or one of the promoters selected from rhenium and alkali metal.

78. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst prepared by a process production of ethylene oxide from ethylene and molecular oxygen which process comprises impregnating a porous refractory support comprising alpha alumina with a catalytically effective amount of silver, a promoting amount of higher alkali metal comprising potassium, rubidium, cesium or mixtures thereof and a promoting amount of rhenium.

79. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising silver, and/or higher alkali metal selected from the group consisting of potassium, rubidium, cesium and mixtures thereof, and/or rhenium wherein the concentration of the silver (measured as the metal) in the solution ranges from about 1 g/l to the solubility limit of silver in the solution, the concentration of alkali metal (measured as the metal) in the solution ranges from about $1 \times 10^{-3}$ g/l to about 12 g/l and the concentration of the rhenium (measured as the metal) ranges from about $5 \times 10^{-3}$ g/l to about 20 g/l to provide the catalyst with a catalytically effective amount of silver, a promoting amount of higher alkali metal and a promoting amount of rhenium.

80. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising solvent having silver compound(s) dissolved therein, and/or higher alkali metal compound(s) selected from compound(s) of potassium, rubidium, cesium and mixtures thereof dissolved therein and/or rhenium-containing compound(s) dissolved therein sufficient to deposit on the support from about 1 to about 25 percent by weight of total catalyst of silver compound(s), measured as the metal, from about 20 to about 1500 ppm by weight of higher alkali metal compound(s), measured as the metal, and from about 0.2 to about 5 millimoles per kilogram of total catalyst of rhenium-containing compound(s), measured as the metal, to provide a catalyst with a catalytically effective amount of silver, a promoting amount of higher alkali metal and a promoting amount of rhenium.

81. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a a process which comprises impregnating a porous, refractory support comprising alpha alumina with one or more solutions comprising silver ions, higher alkali metal ions selected from the group consisting of ions of potassium, rubidium, cesium and mixtures thereof, rhenium-containing ions or mixtures thereof sufficient to deposit on the support from about 1 to about 25 percent by weight of total catalyst of silver, from about 20 to about 1500 parts by weight, measured as the metal, per million parts by weight of total catalyst, of higher alkali metal compound(s) selected from compound(s) of potassium, rubidium, cesium and mixtures thereof, and from about 0.2 to about 5 millimoles of rhenium-containing compound(s), measured as the metal, per kilogram of total catalyst, and after impregnation, reducing the silver on the support to metallic silver to cause the combination of silver, higher alkali metal promoter, rhenium and support to have a higher selectivity to ethylene oxide at a given oxygen conversion level than is obtained under the same reaction conditions with the same combination of silver and support and none or one of the promoters selected from rhenium and higher alkali metal.

82. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support comprising alpha alumina with one or more solutions comprising silver ions, higher alkali metal ions selected from the group consisting of ions of potassium, rubidium, cesium and mixtures thereof, rhenium-containing ions or mixtures thereof sufficient to deposit on the support from about 1 to about 25 percent by weight of total catalyst of silver, from about 20 to about 1500 parts by weight, measured as the metal, per million parts by weight of total catalyst, of higher alkali metal compound(s) selected from compound(s) of potassium, rubidium, cesium and mixtures thereof, and from about 0.2 to about 5 millimoles of a rhenium-containing compound(s), measured as the metal, per kilogram of total catalyst, said rhenium-containing compound(s) providing in the final catalyst rhenium in a form which is extractable in a dilute (20 millimolar) aqueous sodium hydroxide solution; and after impregnation, reducing the silver on the support to metallic silver to cause the combination of silver, higher alkali metal, rhenium and support to have a higher selectivity to ethylene oxide at a given oxygen conversion level than is obtained under the same reaction conditions with the same combination of silver and support and none or one of the promoters selected from rhenium and higher alkali metal.

83. In a process for the production of ethylene oxide wherein ethylene is contacted in the vapor phase with an oxygen-containing gas at ethylene oxide forming conditions at a temperature ranging between about 180° C. and 330° C. in the presence of a silver metal-containing catalyst, the improvement which comprises using a catalyst prepared by a process which comprises impregnating a porous refractory support comprising alpha alumina with a catalytically effective amount of silver, a promoting amount of cesium and a promoting amount of rhenium.

84. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process comprises impregnating a porous refractory support comprising alpha alumina with one or more solutions comprising silver, and/or cesium and/or rhenium wherein the concentration of the silver (measured as the metal) in the solution ranges from about 1 g/l to the solubility limit of silver in the solution, the concentration of cesium (measured as the metal) in the solution ranges from about $1 \times 10^{-3}$ g/l to about 12 g/l and the concentration of the rhenium (measured as the metal) ranges from about $5 \times 10^{-3}$ g/l to about 20 g/l to provide the catalyst with a catalytically effective amount of silver, a promoting amount of cesium and a promoting amount of rhenium.

85. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous refractory support comprising alpha alumina with one or more solutions comprising solvent having silver compound(s) dissolved therein, and/or cesium compound(s) dissolved therein and/or rhenium-containing compound(s) dissolved therein sufficient to deposit on the support from about 1 to about 25 percent by weight of total catalyst of silver compound(s), measured as the metal, from about 20 to about 1500 ppm by weight of cesium compound(s) measured as the metal, and from about 0.2 to about 5 millimoles per kilogram of total catalyst of rhenium-containing compound(s), measured as the metal, to provide the catalyst with a catalytically effective amount of silver, a promoting amount of cesium and a promoting amount of rhenium.

86. In a process for the production of ethylene oxide wherein ethylene is contacted in the vapor phase with an oxygen-containing gas at ethylene oxide forming conditions at a temperature ranging between about 180° C. and 330° C. in the presence of a fixed bed of silver metal-containing catalyst, the improvement which comprises using a catalyst prepared by a process which comprises impregnating a porous, refractory support comprising alpha alumina with one or more solutions comprising solvent silver ions, cesium ions, rhenium-contianing ions or mixtures thereof sufficient to deposit on the support from about 1 to about 25 percent by weight of total catalyst of silver, from about 20 to about 1500 parts by weight, measured as the metal, per million parts by weight of total catalyst, of cesium and from about 0.2 to about 5 millimoles of rhenium-containing compound(s), measured as the metal, per kilogram of total catalyst, and after impregnation, reducing the silver on the support to metallic silver to cause the combination of silver, cesium, rhenium and support to have a higher selectivity to ethylene oxide at a given oxygen conversion level than is obtained under the same reaction conditions with the same combination of silver and support and none or one of the promoters selected from rhenium and cesium.

87. In a process for the production of ethylene oxide wherein ethylene is contacted in the vapor phase with an oxygen-containing gas at ethylene oxide forming conditions at a temperature ranging between about 180° C. and 330° C. in the presence of a fixed of silver metal-containing catalyst, the improvement which comprises using a catalyst prepared by a process which comprises impregnating a porous refractory support comprising alpha alumina with one or more solutions comprising silver ions, cesium ions, rhenium-containing ions or mixtures thereof sufficient to deposit on the support from about 1 to about 25 percent by weight of total catalyst of silver, from about 20 to about 1500 parts by weight, measured as the metal, per million parts by weight of total catalyst, of cesium compound(s), and from about 0.2 to about 5 millimoles of rhenium-containing compound(s), measured as the metal, per kilogram of total catalyst, said rhenium-containing compound(s) providing in the final catalyst rhenium in a form which is extractable in a dilute (20 millimolar) aqueous sodium hydroxide solution; and after impregnation, reducing the silver on the support to metallic silver to cause the combination of silver, cesium, rhenium and support to have a higher selectivity to ethylene oxide at a given oxygen conversion level than is obtained under the same reaction conditions with the same combination of silver and support and none or one of the promoters selected from rhenium and cesium.

88. The process of claims 83, 74, 78, 79, 88 or 84 wherein in the process for preparing the catalyst the amount of silver added by impregnation ranges from about 1 to about 25 percent by weight, the amount of alkali metal added by impregnation ranges from about 20 to about 1500 ppm by weight, measured as the metal, and the amount of rhenium added by impregnation ranges from about 0.2 to about 5 millimoles of rhenium, measured as the metal, per kilogram of total catalyst.

89. The process of claims 73, 74, 78, 79, 83, or 84 wherein in the process for preparing the catalyst the amount of silver found on the catalyst ranges from about 1 to about 25 percent by weight, the amount of alkali metal found on the catalyst ranges from about 20 to about 1500 ppm by weight, measured as the metal, and the amount of rhenium found on the catalyst ranges from about 0.2 to about 5 millimoles of rhenium measured as the metal, per kilogram of total catalyst.

90. The process of claims 73, 74, 78, 79, 83 or 84 wherein in the process for preparing the catalyst the amount of silver found on the surface of the support ranges from about 1 to about 25 percent by weight, the amount of alkali metal found on the surface of the support ranges from about 20 to about 1500 ppm by weight, measured as the metal, and the amount of rhenium found on the surface of the support ranges from about 0.2 to about 5 millimoles of rhenium, measured as the metal, per kilogram of total catalyst.

91. The process of claims 73, 74, 75, 78, 79, 80, 83, 84 or 85 wherein in the process for preparing the catalyst after impregnation the silver is reduced to metallic silver.

92. The process as in any of claims 73-87 wherein in the process for preparing the catalyst after impregnation the silver is reduced to metallic silver by heating at a temperature between about 75° C. to about 400° C.

93. The process as in any of claims 73-87 wherein in the process for preparing the catalyst after impregnation the silver is reduced to metallic silver by heating at a temperature between about 50° C. to about 600° C.

94. The process of claims 74, 75, 76, 77, 79, 80, 81, 82, 84, 85, 86 or 87 wherein in the process for preparing the catalyst the solution containing silver also comprises water and vicinal alkylenediamine(s) of from 2 to 4 carbon atoms.

95. The process of claims 74, 75, 76, 77, 79, 80, 81, 82, 84, 85, 86 or 87 wherein in the process for preparing the catalyst the solution containing silver also comprises water and ethylenediamine.

96. The process of claims 74, 75, 76, 77, 79, 80, 81, 82, 84, 85, 86 or 87 wherein in the process for preparing the catalyst the solution containing silver also comprises water, vicinal alkalinediamine(s) of from 2 to 4 carbon atoms and vicinal alkanolamine(s) of from 2 to 4 carbon atoms.

97. The process of claims 74, 75, 76, 77, 79, 80, 81, 82, 84, 85, 86 or 87 wherein the solution containing silver also comprises water, ethylenediamine and monoethanolamine.

98. The process of claims 75, 80 or 85 wherein in the process for preparing the catalyst the silver compound is selected from silver oxalate, silver oxide, silver carbonate, silver lactate and mixtures thereof.

99. The process of claims 75, 80 or 85 wherein in the process for preparing the catalyst the alkali metal compound is a hydroxide and/or a nitrate.

100. The process of claims 75, 80 or 85 wherein in the process for preparing the catalyst the rhenium-containing compound is rhenium heptoxide or ammonium and/or alkali metal perrhenate.

101. The process of claims 76, 77, 81, 82, 86 or 87 wherein in the process for preparing the catalyst the rhenium-containing ions are perrhenate ions.

102. The process of claims 76, 77, 81, 82, 86 or 87 wherein in the process for preparing the catalyst the selectivity is measured at an oxygen conversion of about 40% at a gas hourly space velocity of about 3300 and when the catalyst has been placed onstream for about 16±4 hours.

103. The process of claims 1, 17, 18, 58, 73, 78 or 83 wherein in the catalyst or in the process for preparing the catalyst the support has a surface area ranging from about 0.05 to about 10 $m^2/g$.

* * * * *